(12) United States Patent
Damazo et al.

(10) Patent No.: US 10,286,241 B2
(45) Date of Patent: May 14, 2019

(54) COMBUSTION ARRESTER QUANTIFICATION SYSTEMS AND METHODS

(71) Applicants: The Boeing Company, Chicago, IL (US); King Abdullah University of Science and Technology, Thuwal (SA)

(72) Inventors: Jason Scott Damazo, Seattle, WA (US); Deanna A. Lacoste, Makkah (SA); Eddie Kwon, Seattle, WA (US); William Lafayette Roberts, IV, Appleton, WI (US)

(73) Assignee: The Boeing Company, Chicago, IL (US)

( * ) Notice: Subject to any disclaimer, the term of this patent is extended or adjusted under 35 U.S.C. 154(b) by 58 days.

(21) Appl. No.: 15/472,039

(22) Filed: Mar. 28, 2017

(65) Prior Publication Data

US 2018/0280746 A1  Oct. 4, 2018

(51) Int. Cl.
| | | |
|---|---|---|
| *A62C 4/00* | (2006.01) | |
| *A62C 4/02* | (2006.01) | |
| *A62C 37/50* | (2006.01) | |
| *B01J 19/00* | (2006.01) | |

(Continued)

(52) U.S. Cl.
CPC ............... *A62C 37/50* (2013.01); *A62C 4/00* (2013.01); *A62C 4/02* (2013.01); *G01N 33/0036* (2013.01); *B01J 19/002* (2013.01); *F23D 14/82* (2013.01)

(58) Field of Classification Search
CPC .. A62C 37/50; A62C 4/00; A62C 4/02; G01N 33/0036; B01J 19/002; F23D 14/82
See application file for complete search history.

(56) References Cited

U.S. PATENT DOCUMENTS

| | | |
|---|---|---|
| 3,434,336 A | 3/1969 | Harr |
| 4,909,730 A | 3/1990 | Roussakis et al. |

(Continued)

FOREIGN PATENT DOCUMENTS

| | | |
|---|---|---|
| EP | 0375455 | 6/1990 |
| JP | 2014000258 | 1/2014 |
| KR | 101448867 | 10/2014 |

(Continued)

OTHER PUBLICATIONS

Mecke, S., et al. "Examination of the Flame Transmission Through Porous Structures." International Journal of Transport Phenomena 10.3 (2008).*

(Continued)

*Primary Examiner* — Jonathan M Dunlap
(74) *Attorney, Agent, or Firm* — Dascenzo Intellectual Property Law, P.C.

(57) ABSTRACT

Systems and methods for quantifying combustion arrester performance are disclosed. Methods include filling an upstream volume and a combustion arrester with a flammable gas, igniting the flammable gas in the upstream volume (and upstream of the combustion arrester), measuring a composition of gas discharged from the combustion arrester due to ignition of the flammable gas, and quantifying the performance of the combustion arrester based on the composition of gas measured. The measured gas composition may include types and/or amounts of combustion species within the gas discharged from the combustion arrester.

22 Claims, 7 Drawing Sheets

(51) Int. Cl.
*F23D 14/82* (2006.01)
*G01N 33/00* (2006.01)

(56) References Cited

U.S. PATENT DOCUMENTS

| 5,415,233 | A | 5/1995 | Roussakis et al. | |
| 2009/0277655 | A1* | 11/2009 | DeCourcy | B01J 8/06 169/45 |

FOREIGN PATENT DOCUMENTS

| WO | WO 94/00197 | 1/1994 |
| WO | WO 2016/181170 | 11/2016 |

OTHER PUBLICATIONS

Asano, Seiichiro, et al. "Visualization of behaviors of a propagating flame quenching for hydrogen-air gas mixture." Journal of visualization 13.2 (2010): 107-119.*

Werling, Lukas, et al. "Experimental investigation of the ignition, flame propagation and flashback behavior of a premixed green propellant consisting of N2O and C2H4." 7th European Conference for Aeronautics and Space Sciences. 2017.*

Kersten, Christoph, and Hans Förster. "Investigation of deflagrations and detonations in pipes and flame arresters by high-speed framing." Journal of loss prevention in the process industries 17.1 (2004): 43-50.*

"Laser-induced fluorescence (LIF)," Lund University. 1 page. Nov. 5, 2015. Accessed online on Jul. 9, 2018 at <http://www.forbrf.lth.se/english/research/measurement-methods/laser-induced-fluorescence-lif/>.*

"Visualization of radicals," Lund University. pp. 1-2. Nov. 5, 2015. Accessed online on Jul. 9, 2018 at <http://www.forbrf.lth.se/english/research/measurement-methods/laser-induced-fluorescence-lif/visualization-of-radicals/>.*

Grisch, Frédéric, and Mikaël Orain. "Role of Planar Laser-Induced Fluorescence in Combustion Research." AerospaceLab 1 (2009): p. 1-14.*

"Flame Arrestor Technology," Emerson Process Management Regulator Technologies Tulsa, LLC (undated) accessed at http://www.enardo.com/pdfs/tech_paper_fat.pdf.

"Flame Arresters," Civil Eng. Handbook (2015) accessed at http://www.civilengineeringhandbook.tk/process-safety/flame-arresters.html.

Lecklider, "Shake, Bake, and Boom Tests Verify Performance," Evaluation Eng. (2011) accessed at http://www.evaluationengineering.com/shake-bake-and-boom-tests-verify-performance.

Roussakis, "A Comprehensive Test Method for Inline Flame Arresters," Westech Industrial Ltd. (1988).

Thomas, et al., "Testing Procedures for Explosion Arresters: Some Problems and Potential Solutions," ICHEME Symposium Series No. 139 (1995) p. 113.

Wilson, et al., "Performance of Commercially Available Flame Arrestors for Butane/Air and Gasoline/Air Mixtures," U.S. Coast Guard Report No. CG-D-72-78 (1978).

Yang, et al., "Effect of Pressure on Effectiveness of Quenching Meshes in Transmitting Hydrogen Combustion," Nuc. Eng. Design 224 (2003) p. 199.

European Patent Office, Extended European Search Report for related European Application No. 17208250, dated Jul. 2, 2018.

Thomas et al., An Evaluation of New Procedures for Testing Explosion Arresters, Institution of Chemical Engineers, Trans IChemE, vol. 76, Part B, pp. 277-285, Nov. 1998.

Machine-generated English abstract of JP 2014000258, downloaded from Espacenet.com Aug. 22, 2018.

Machine-generated English abstract of KR 101448867, downloaded from Espacenet.com Aug. 22, 2018.

* cited by examiner

COMBUSTION ARRESTER QUANTIFICATION SYSTEMS AND METHODS

FIELD

The present disclosure relates to combustion arrester quantification systems and methods.

BACKGROUND

Combustion arresters are used to protect people and equipment in many industries such as fuel production, mining, transportation, chemical processing, power generation, and wastewater treatment. For example, combustion arresters may be used to avoid undesired combustion during fuel handling such as in conjunction with storage, transport, consumption, and production of fuel (e.g., natural gas, gasoline, diesel fuel, jet fuel, etc.).

Combustion arresters are installed in systems that interact with gases that may be flammable. Combustion arresters are designed to prevent combustion in one part of the system from igniting nearby flammable gases. Combustion arresters generally include a permeable quenching element enclosed in a housing. The permeable element permits gas to flow but has small passages that are arranged to cool the burning gas of a combustion front to below the autoignition temperature of the gas. Some combustion arresters also may significantly attenuate the pressure wave or shock wave associated with the combustion front.

Design and performance of combustion arresters are dependent on operating conditions, including the type of flammable gas and the temperature, pressure, volume, and flow rate of the flammable gas. Because of the myriad of conditions that may affect performance and the generally unpredictable nature of combustion fronts, a combustion arrester suitable for one situation may not be suitable for another.

Testing of combustion arresters typically involves testing the combustion arrester in the particular circumstances of the expected use. That is, combustion arrester testing generally is a system test (involving actual system components) rather than merely a component test of the combustion arrester. For example, the location of the combustion arrester relative to potential ignition sources and/or flammable gas sources, the size of piping to and/or from the combustion arrester, the type of flammable gas, the temperature and/or pressure of system operation, and the type of ignition sources all may affect the performance of a combustion arrester in a system. To produce reliable results, combustion arrester testing commonly incorporates much, if not all, of the final system components. Especially for large and/or complex installations, reproducing the final design while testing a component of the final design (the combustion arrester) may be a slow and expensive process.

In conventional combustion arrester testing, combustion fronts with different flame propagation conditions are produced (often with as much of the final installation components as possible) to determine if the combustion arrester stops (or does not stop) the particular combustion front. A typical test regime may involve repeating a test several times to verify that the combustion arrester may repeatably stop a combustion front in the given scenario. Such repetitive testing may require rebuilding the test system and/or replacing the combustion arrester for each test run.

Flame speed and combustion front pressure changes may be controlled to some extent by adjusting the length and/or complexity of piping between the combustion arrester and ignition source. Generally, longer pipe lengths lead to faster flame velocities. Additionally or alternatively, a combustion front may be accelerated by introducing specific flame acceleration structures such as a Shchelkin spiral or a series of annular disks. Elbows and tees in the piping also may serve to accelerate a combustion front. Generally, flame acceleration is achieved by increasing turbulence in the gas at the combustion front. Increased turbulence tends to increase combustion, leading to higher pressures (e.g., due to more heating of the burnt gas) and higher combustion front speeds. A combustion front may travel as a deflagration wave (the flame speed is less than the speed of sound in the unburnt gas downstream of the front) or a detonation wave (the flame speed is greater than or equal to the speed of sound in the unburnt gas downstream of the front). In some conditions, a combustion front may transition from a deflagration wave to a detonation wave in what is referred to as a deflagration to detonation transition. During the deflagration to detonation transition, the pressure and flame speed may be much greater than in a detonation wave. The type of combustion front and the flame speed are intimately affected by the particulars of the system design. Additionally, a combustion arrester that may stop an intense detonation wave may not adequately stop a less intense deflagration wave (or vice versa).

As an example of a complicated system, large aircraft typically use combustion arresters in the vent tubes of fuel tanks. To certify and test such configurations, all or most of the aircraft's fuel system may be reproduced (testing in situ). During the design of new systems, the test of the combustion arrester may require finalized components before the design itself is finalized. Further, even successful tests (where the combustion arrester stopped the combustion front) may need to be reproduced (or reproduced under similar conditions) to verify that the performance of the combustion arrester will be reliably successful.

SUMMARY

Systems and methods for quantifying combustion arrester performance are disclosed. Methods include filling an upstream volume and a combustion arrester with a flammable gas, igniting the flammable gas in the upstream volume (and upstream of the combustion arrester), measuring a composition of gas discharged from the combustion arrester due to ignition of the flammable gas, and quantifying the performance of the combustion arrester based on the composition of gas measured. The measured gas composition may include types and/or amounts of combustion species within the gas discharged from the combustion arrester.

Systems include a combustion arrester, an ignition source (upstream from the combustion arrester), and a sensor system with a sensed volume downstream from the combustion arrester. The sensor system is configured to measure the composition of gas discharged from the downstream end of the combustion arrester. The sensor system may include apparatuses that use optical techniques and/or gas sampling techniques to measure the gas composition.

DESCRIPTION

Figure 1:
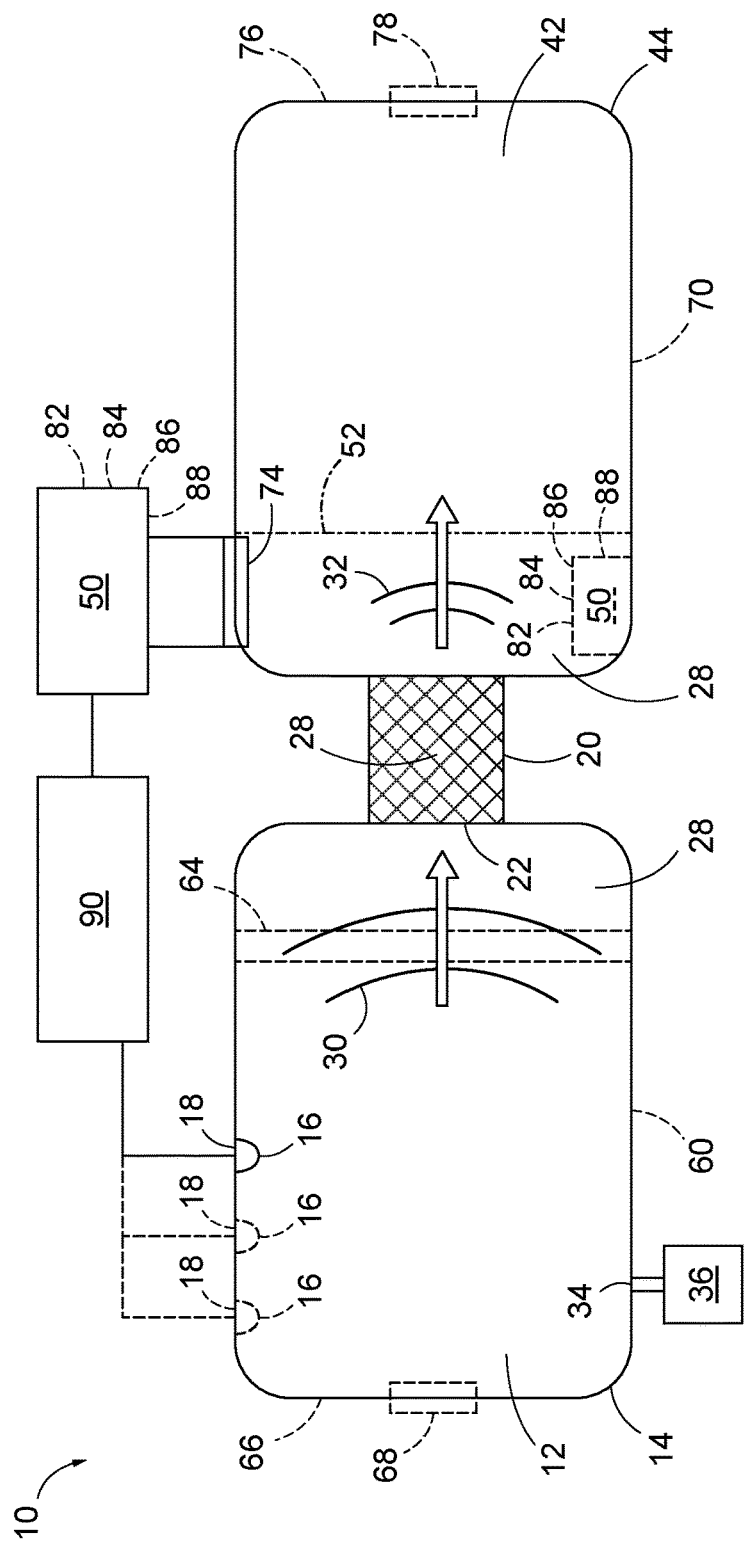
FIG. 1 is a schematic representation of a test system for combustion arresters according to the present disclosure.

Combustion arrester quantification systems and methods of the present disclosure may be used to determine the effectiveness of combustion arresters to stop combustion fronts. The disclosed systems and methods may be used to quantify the effectiveness of the combustion arrester under test, yielding more than a binary outcome (i.e., not just whether the combustion arrester under test succeeded or failed to stop the combustion front). Quantitative measures may be obtained by analyzing the chemical composition of the gas that passes through the combustion arrester. Quantitation may be enhanced by measuring gas temperature and/or gas velocity. Additionally or alternatively, quantitation of the effectiveness of the combustion arrester may be measured by analyzing the spatially-resolved gas temperature, velocity and/or chemical composition of gas that passes through the combustion arrester. Spatially-resolved measurements may include cross sectional profiles of the gas flow downstream of the combustion arrester and/or two-dimensional projections of the gas flow downstream of the combustion arrester. Quantitation of combustion arrester efficacy permits different combustion arresters to be compared directly in a given design and permits more streamlined and/or directed testing of combustion arresters. For example, replication of successful combustion arrester tests (in which the combustion arrester successfully stopped the combustion front) may not be necessary for tests in which the quantitative efficacy indicates sufficient operating margin. As another example, fewer testing conditions may be needed because quantitative efficacy may better predict effectiveness in alternate conditions.

Moreover, the disclosed systems and methods may define reproducible conditions to test combustion arresters that may be tuned to replicate normal and/or worse case combustion fronts that may be experienced in installed configurations. For example, systems and methods may configure upstream and/or downstream volumes, ignition source location, combustion front flame speed, and/or gas flow conditions (e.g., turbulent or laminar flow) with standardized testing components. The standardized components may be arranged to produce conditions equivalent to those of the final installed configuration (in analog to using an equivalent circuit for electrical testing and analysis). The standardized components may reduce the size and/or complexity of test systems relative to convention test systems. By using standardized components, the desired test conditions may be reliably reproduced between test runs (of the same or different test regiments) and/or for different combustion arresters.

FIGS. 1-8 illustrate combustion arrester test systems and methods, and components thereof. In general, in the drawings, elements that are likely to be included in a given embodiment are illustrated in solid lines, while elements that are optional or alternatives are illustrated in dashed lines. However, elements that are illustrated in solid lines are not essential to all embodiments of the present disclosure, and an element shown in solid lines may be omitted from a particular embodiment without departing from the scope of the present disclosure. Elements that serve a similar, or at least substantially similar, purpose are labelled with numbers consistent among the figures. Like numbers in each of the figures, and the corresponding elements, may not be discussed in detail herein with reference to each of the figures. Similarly, all elements may not be labelled or shown in each of the figures, but reference numerals associated therewith may be used for consistency. Elements, components, and/or features that are discussed with reference to one or more of the figures may be included in and/or used with any of the figures without departing from the scope of the present disclosure.

FIG. 1 is a schematic representation of a test system 10 for a combustion arrester 20. The test system 10 includes an upstream volume 12 and a downstream volume 42 with the combustion arrester 20 between. The combustion arrester 20 has an upstream end 22 in fluidic contact with the upstream volume 12 and a downstream end 24 in fluidic contact with the downstream volume 42. The upstream volume 12 may be enclosed and/or defined by an upstream chamber 14. The upstream chamber 14 may be directly connected to the combustion arrester 20 or may otherwise terminate at the upstream end 22 of the combustion arrester 20. The downstream volume 42 may be enclosed and/or defined by a downstream chamber 44. The downstream chamber 44 may be directly connected to the combustion arrester 20 or may otherwise terminate at the downstream end 24 of the combustion arrester 20.

In use, the test system 10 may contain and/or be filled with flammable gas 28 (the flammable gas 28 may flow through the test system 10). The flammable gas 28 is a gas that is flammable and configured to be ignited in the upstream volume 12 (e.g., by an ignition source 16). Ignition of the flammable gas 28 causes a combustion front 30 in the upstream volume 12 that propagates to the upstream end 22 of the combustion arrester 20. The combustion front 30 (also referred to as a flame front and/or a combustion wave) includes combusting gas of the flammable gas 28. Generally, in front of the combustion front 30 (toward the downstream side) are uncombusted reactants in the flammable gas 28. Behind the combustion front 30 (toward the upstream side) are combustion products. The combustion front 30 may leave behind partial combustion products and/or combustion reactants, depending on the dynamics of the combustion, the geometry of the upstream volume 12, the concentration of the combustion reactants, the type of combustion reactants, the temperature of the flammable gas 28, the temperature of the walls enclosing the upstream volume 12 (e.g., the temperature of the upstream chamber 14), the pressure of the flammable gas 28, etc.

The flammable gas 28 includes a combustion fuel and a combustion oxidant in a mixture that is flammable in the conditions of the upstream volume 12 before ignition. Combustion is a reaction between the combustion fuel and combustion oxidant accompanied by the release of heat. Examples of combustion fuels include hydrocarbon fuels, hydrogen, methane, propane, ethylene, gasoline, diesel fuel, and jet fuel. A common gaseous combustion oxidant is molecular oxygen. The flammable gas 28 may include other chemical constituents such as inert components and/or components of air generally called diluents). For example, the flammable gas 28 may be a mixture of ethylene in air. Products of combustion depend on the reactants (i.e., the combustion fuel and combustion oxidant) and may include carbon dioxide and water. Carbon dioxide and water are complete combustion products of hydrocarbon fuels with oxygen. Incomplete combustion and/or reaction with various gas components may produce species (partial combustion products) such as carbon monoxide, formaldehyde, hydroxyl radicals, hydrogen, and/or methanol. Products of combustion also may include products of reactions other than the combustion fuel-combustion oxidant reaction (e.g., combustion in air may produce nitrogen oxides, i.e., nitric oxide and/or nitrous oxide).

The combustion arrester 20 generally affects the combustion front 30 as the gas of the combustion front 30 passes through the combustion arrester 20. The combustion arrester 20 may or may not quench the combustion front 30. If the combustion arrester 20 performs adequately for the given conditions, the combustion arrester 20 completely quenches the combustion front 30. The combustion front 30, as modified by the effects of the combustion arrester 20 is emitted from the downstream end 24 of the combustion arrester 20 as discharged gas 32. The discharged gas 32 may be combusting (in which case, the combustion arrester 20 was not sufficiently effective), may be in a state with sufficient energy to ignite the flammable gas 28 in the downstream volume 42 (in which case, the combustion arrester 20 was not sufficiently effective), or may be in a state lacking sufficient energy to ignite the flammable gas 28 in the downstream volume 42 (in which case, the combustion arrester 20 was sufficiently effective). Sufficient energy to ignite the flammable gas 28 in the downstream volume 42 may be from a combination of one or more of temperature of the discharged gas 32, reactive chemical species in the discharged gas 32, and a pressure impulse (e.g., a shock wave) associated with the discharged gas 32. If the discharged gas 32 is sufficiently cool, sufficiently devoid of reactive chemical species, and/or has sufficiently low pressure, the discharged gas 32 may not ignite the flammable gas 28 in the downstream volume 42.

The combustion arrester 20 is the component to be tested in the test system 10 and may be referred to as the component under test and/or the combustion arrester under test. The combustion arrester 20 may be a flame arrester, a flame trap, a deflagration arrester, and/or a detonation arrester. Generally, the combustion arrester 20 has an internal fluid path to permit gas to flow from the upstream end 22 to the downstream end 24 (and generally vice versa). In the fluid path, the combustion arrester 20 includes a permeable quenching element (such as mesh, ribbons, wires, and/or particulate) that define small passages for gas flow and that are configured to quench the combustion front 30 traversing the combustion arrester 20 from the upstream end 22 to the downstream end 24. Generally, the permeable element of the combustion arrester 20 is configured to cool the combustion front 30, to impede diffusion of reactive species of the combustion front 30, and/or to slow the combustion front 30 so that the gas of the combustion front 30 ceases to have enough energy to produce self-propagating combustion (e.g., the gas of the combustion front 30 is cooled below the autoignition temperature). The effectiveness of a combustion arrester 20 may be dependent on the temperature, pressure, velocity, and chemical composition of the combustion front 30, the chemical composition of the flammable gas 28 upstream and downstream of the combustion arrester 20, the pressure, temperature, and volume of the gas in the downstream volume 42, and the internal design of the combustion arrester 20.

Upstream and downstream as used herein are relative to the propagating combustion front 30 that may be impeded by the combustion arrester 20. The upstream volume 12 and the upstream end 22 may be referred to respectively as the unprotected volume and the unprotected end. The downstream volume 42 and the downstream end 24 may be referred to respectively as the protected volume and the protected end.

The upstream chamber 14 defines the upstream volume 12 and generally is configured to direct the combustion front 30 to the upstream end 22 of the combustion arrester 20. The upstream chamber 14 may include, and/or may be formed of, components of the actual production system that is upstream of the combustion arrester 20 when the combustion arrester 20 is deployed. Additionally or alternatively, the upstream chamber 14 may include, and/or may be formed of, standardized components to facilitate testing (e.g., one or more modular upstream shell sections 60 as discussed further herein). The upstream chamber 14 generally is axisymmetric and/or formed of axisymmetric components, in particular when standardized components are used.

The upstream chamber 14 may define a closed volume (which the flammable gas 28 is contained in) or an open volume (which the flammable gas 28 may flow into or out of). In some embodiments, the upstream chamber 14 may include a pressure relief device 68 such as a pressure relief valve or a burst diaphragm that is configured to release excess pressure (e.g., by opening or rupturing) in the upstream chamber 14. A burst diaphragm is a diaphragm or membrane that is thin enough to rupture at a designed pressure differential across the diaphragm or membrane. The pressure relief device 68 may be configured to contain the flammable gas 28 at nominal pressure (e.g., before the flammable gas 28 is ignited and begins combusting) and to breach the containment of the flammable gas 28 upon combustion, deflagration, and/or detonation in the upstream chamber 14. In such an embodiment, the upstream chamber 14 may provide a closed volume before ignition and may provide an open volume after ignition. Providing a closed volume before ignition may be useful to avoid leakage of the flammable gas 28 from the test system 10. Providing an open volume after ignition may be useful to simulate combustion conditions that may occur in the expected use of the combustion arrester 20 (e.g., a large upstream volume in use).

An open or closed upstream volume 12, the volume of the upstream chamber 14, the pressure of the flammable gas 28, the temperature of the flammable gas 28 and/or the upstream chamber 14, and the internal geometry of the upstream chamber 14 may affect the combustion front 30 formed by igniting the flammable gas 28 and the performance of the combustion arrester 20.

The upstream chamber 14 may be configured to withstand activation of the ignition source 16 and/or combustion (e.g., deflagration and/or detonation) of the flammable gas 28 within the upstream chamber 14. The upstream chamber 14 may be undamaged by such events or may be configured to breach in a controlled manner (e.g., by operation of the pressure relief device 68). For example, the pressure relief device 68 may be configured to protect the upstream chamber 14 from damaging combustion and/or detonation by relieving pressure within the upstream chamber 14 before the upstream chamber 14 would otherwise be damaged.

The upstream chamber 14 includes at least one ignition port 18 to accept the ignition source 16. When the ignition source 16 is installed in the ignition port 18, the ignition source 16 (at least the active portion of the ignition source 16) is in the upstream volume 12 and the upstream chamber 14. The upstream chamber 14 may include a series of ignition ports 18 such that the ignition source 16 may be installed in any one of the ignition ports 18. The upstream chamber 14 may have more than one ignition source 16 installed (e.g., in different ignition ports 18). However, for initiating a single test, typically a single ignition source 16 is activated (even if more than one ignition source 16 is installed in the upstream chamber 14). Unused ignition ports 18 may be sealed (e.g., with a cover or an unused ignition source).

The ignition source 16 is a device that is configured to ignite the flammable gas 28 when the ignition source 16 is activated. The ignition source 16 is selectively activated to cause the flammable gas 28 in the upstream volume 12 to ignite and form the combustion front 30. Examples of ignition sources 16 include an electrical arc device (e.g., a spark plug) and/or an explosive (e.g., a blasting cap, a high yield explosive). The location of the ignition source 16 (within the upstream chamber 14 and/or with respect to the combustion arrester 20), the type of ignition source 16, and/or the energy released by the ignition source 16 may affect the combustion front 30 and/or the performance of the combustion arrester 20.

The upstream chamber 14 may include at least one gas port 34. The gas port 34 may be configured to fill the upstream chamber 14, the combustion arrester 20, and/or the downstream chamber 44 with the flammable gas 28. The gas port 34 may be configured to flow flammable gas 28 through the upstream chamber 14, the combustion arrester 20, and/or the downstream chamber 44. The gas port 34 may be configured to evacuate and/or purge the upstream chamber 14, the combustion arrester 20, and/or the downstream chamber 44 of flammable gas 28. Each gas port 34 may be dedicated to one or more functions such as filling, flowing, purging, and/or evacuating and may include and/or be associated with a valve to control gas flow through the gas port 34 (e.g., a one-way valve, a shut-off valve, or a proportional valve). One or more gas ports 34 may be located in the downstream chamber 44, in addition to or alternate to gas ports 34 located in the upstream chamber 14.

The gas port(s) 34 may be configured to convey gas from at least one gas source 36. The gas source 36 may be a source of flammable gas 28. Additionally or alternatively, each gas source 36 may be a source of one or more components of the flammable gas 28. For example, one gas source 36 may include a combustion fuel (e.g., ethylene) and another source may include a combustion oxidant (e.g., air). The gas components may be mixed (to form the flammable gas 28) in the upstream chamber 14, the combustion arrester 20, and/or the downstream chamber 44. Additionally or alternatively, the gas components may be mixed (to form the flammable gas 28) prior to introduction into the upstream chamber 14, the combustion arrester 20, and/or the downstream chamber 44. The gas source 36 may be a vessel or cylinder of compressed gas, may include gas generation devices (e.g., chemical production of gaseous components), and/or may include a pump, a compressor, and/or a blower.

The downstream chamber 44 defines the downstream volume 42 and generally is configured to receive the discharged gas 32 from the downstream end 24 of the combustion arrester 20. The downstream chamber 44 may include, and/or may be formed of, components of the actual production system that is downstream of the combustion arrester 20 when the combustion arrester 20 is deployed. Additionally or alternatively, the downstream chamber 44 may include, and/or may be formed of, standardized components to facilitate testing (e.g., one or more modular downstream shell sections 70 as discussed further herein).

The downstream chamber 44 may define a closed volume (which the flammable gas 28 is contained in) or an open volume (which the flammable gas 28 may flow into or out of). In some embodiments, the downstream chamber 44 may include a pressure relieve device 78 such as described with respect to the pressure relief device 68 (e.g., a pressure relief valve or a burst diaphragm). The pressure relief device 78 is configured to release excess pressure in the downstream chamber 44. The pressure relief device 78 may be configured to contain the flammable gas 28 at nominal pressure (e.g., before the discharged gas 32 enters the downstream chamber 44) and to breach the containment of the flammable gas 28 upon combustion, deflagration, detonation, and/or sufficient pressure rise in the downstream chamber 44. In such an embodiment, the downstream chamber 44 may provide a closed volume before ignition in the upstream volume 12 (e.g., to contain the flammable gas 28) and may provide an open volume after ignition in the downstream volume 42 (e.g., to simulate a large downstream volume in use).

An open or closed downstream volume 42, the volume of the downstream chamber 44, the temperature of the downstream chamber 44, and the internal geometry of the downstream chamber 44 may affect the combustion front 30, the discharged gas 32, and the performance of the combustion arrester 20.

The downstream chamber 44 may be configured to withstand combustion (e.g., deflagration and/or detonation) of the flammable gas 28 within the downstream chamber 44. The downstream chamber 44 may be undamaged by such events or may be configured to breach in a controlled manner (e.g., by operation of the pressure relief device 78). For example, the pressure relief device 78 may be configured to protect the downstream chamber 44 from damaging combustion and/or detonation by relieving pressure within the downstream chamber 44 before the downstream chamber 44 would otherwise be damaged.

Figure 2:
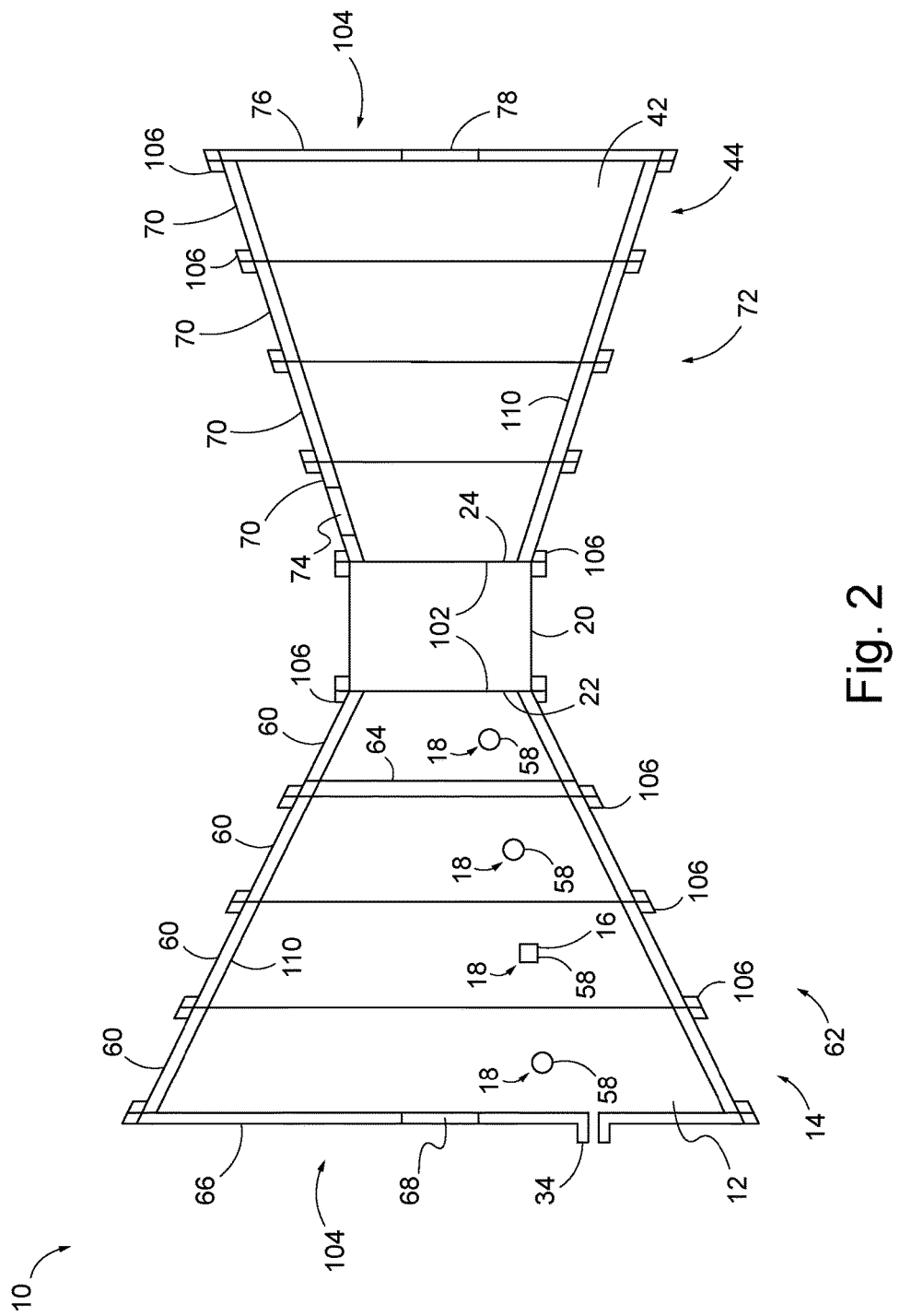
FIG. 2 is a schematic representation of an example of a test system for combustion arresters according to the present disclosure.

As shown in FIG. 2, the upstream chamber 14 and/or the downstream chamber 44 may include features to facilitate testing of the combustion arrester 20 in a standardized, reconfigurable, and/or compact manner. For example, the upstream chamber 14 may include a convergent duct 62 and/or the downstream chamber 44 may include a divergent duct 72. Additionally or alternatively, the upstream chamber 14 may include at least one modular upstream shell section 60 and/or the downstream chamber 44 may include at least one modular downstream shell section 70.

The interior shape of the upstream chamber 14 may affect the propagation of the combustion front 30. Generally, as the combustion front 30 propagates toward the upstream end 22 of the combustion arrester 20, the combustion front 30 increases the heat and pressure of the gas in the upstream chamber 14 (in particular at the location of the combustion front 30). The temperature increase contributes to pressure increase behind (upstream of) the combustion front 30. The pressure increase due to combustion in the upstream chamber 14 may be referred to as overpressure. The velocity of the combustion front 30 with respect to the surrounding gas (i.e., the flammable gas 28 that is downstream and unaffected by the combustion front 30) is called the burning velocity (or burning speed) of the combustion front 30. The velocity of the combustion front 30 relative to external coordinates (e.g., the test system 10 or the upstream chamber 14) is called the flame velocity (or flame speed). If the flammable gas 28 has a net flow, the flame velocity is different than the burning velocity.

Generally, the burning velocity of the combustion front 30 increases as the combustion front 30 travels down a smooth pipe. Factors that contribute to the acceleration include the generated heat, the generated pressure, and turbulence induced by viscous interactions within the gas and between the gas and pipe wall. At high enough burning velocity, the deflagration of a combustion front (i.e., propagation of the combustion front by heat and supply of active chemical species to the unburnt gas downstream of the combustion front) may transition to a detonation (i.e., propagation of the combustion front by shock compression of the unburnt gas). In conventional testing, a very long pipe (e.g., greater than 5 meters) may be used to achieve high burning velocities and/or detonation.

Figure 3:
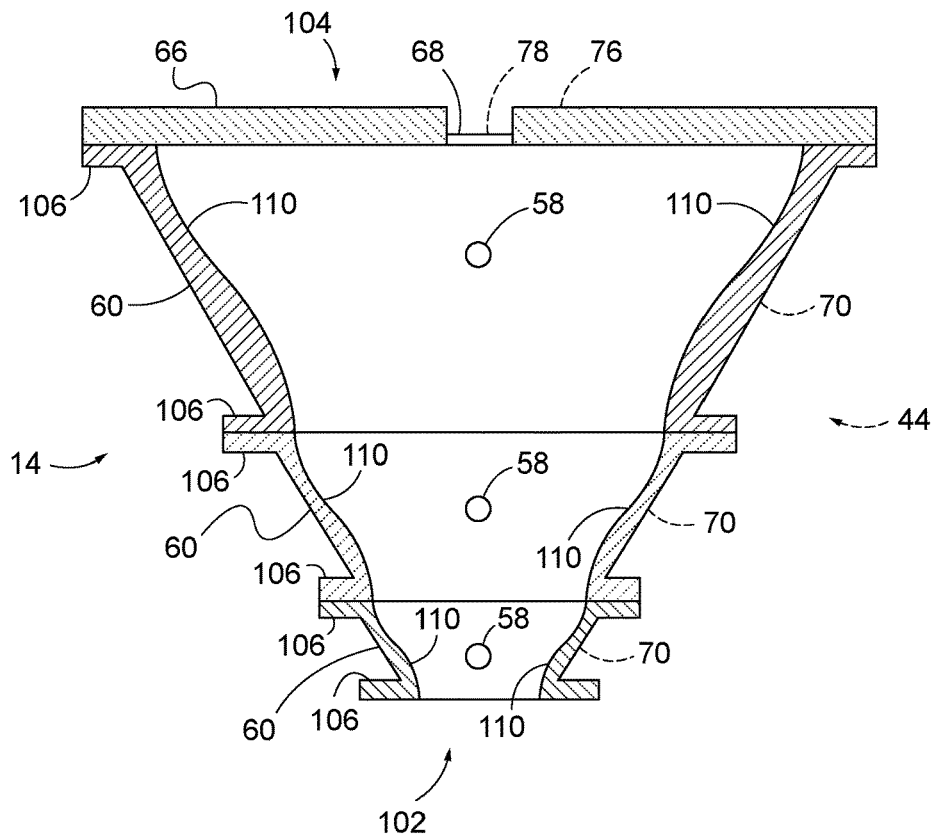
FIG. 3 is a cross sectional view of an example of a chamber for combustion arrester testing according to the present disclosure.

In the test system 10, the interior of the upstream chamber 14 may define the convergent duct 62. The convergent duct 62 may direct and/or accelerate the combustion front 30 as the combustion front 30 propagates down the convergent duct 62 to the combustion arrester 20. The convergent duct 62 is a region of the upstream chamber 14 that has a decreasing cross sectional area as a function of decreasing distance to the downstream end of the convergent duct 62. The downstream end of the convergent duct 62 has a smaller cross sectional area than the upstream end of the convergent duct 62. The downstream end of the convergent duct 62 is at or proximate to the upstream end 22 of the combustion arrester 20. For example, the convergent duct 62 may terminate at the upstream end 22 of the combustion arrester 20. In FIGS. 2 and 3, the smaller end 102 of the convergent duct 62 is the downstream end and the larger end 104 of the convergent duct 62 is the upstream end.

As the combustion front 30 traverses the convergent duct 62 toward the combustion arrester 20, the cross sectional area decreases and contributes to increasing the pressure associated with the combustion front 30. The decreasing cross sectional area and increasing pressure may contribute to accelerating the combustion front 30 and/or producing a detonation in the combustion front 30. Use of the convergent duct 62 may facilitate a more compact test system 10 (without the need for a long upstream pipe to produce the same combustion front speed) and/or a more reliable combustion front propagation speed (with the burning velocity predominately influenced by the convergence of the convergent duct 62 rather than viscous interactions with the interior of the upstream chamber 14).

As indicated in the cross sectional view of FIG. 3, modular upstream shell sections 60 are shells that, together (with or without other components), may form the hollow body of the upstream chamber 14. The interior profiles 110 of the upstream chamber 14 and/or the individual modular upstream shell sections 60 (if present) may be configured to reduce turbulence and/or to encourage laminar flow (e.g., top-hat flow) through the upstream chamber 14 to the combustion arrester 20 (or at least through the convergent duct 62). In laminar flow, streamlines of flow generally do not cross and mixing in the flow is generally diffusion dominated. In top-hat flow (also referred to as plug flow), the velocity profile (perpendicular to the net flow direction) is substantially uniform, with boundary effects limited to generally thin sections near the walls that confine the flow. In turbulent flow, streamlines may fold and/or mix. In the combustion front 30, laminar flow may encourage slower combustion and burning velocity while turbulent flow may encourage faster mixing, combustion, and burning velocity.

Examples of interior profiles 110 that may reduce turbulence and/or encourage laminar flow are shown the cross sectional view of FIG. 3. An example of a profile for an axisymmetric convergent duct may be defined by:

$$P(x) = \frac{D_1}{2\left[1-\left(1-\left(\frac{D_1}{D_2}\right)^2\right)\left(1-\frac{(L-x)^2}{L^2}\right)^2\left(1+\frac{(L-x)^2}{3L^2}\right)^{-3}\right]^{1/2}} \quad \text{Eq. 1}$$

where x is the axial coordinate, P(x) is profile radius as a function of axial position, $D_1$ is the smallest diameter of the profile (e.g., the smaller (downstream) end 102 of the convergent duct 62), $D_2$ is the largest diameter of the profile (e.g., the larger (upstream) end 104 of the convergent duct 62), and L is the axial length of the profile (e.g., the axial distance between the smaller end 102 and the larger end 104). In the example of FIG. 3, each of the modular upstream shell sections 60 has the same interior profile 110 as given by Eq. 1.

The interior profiles 110 of the modular upstream shell sections 60 generally are configured such that there is little to no discontinuity at the interior joint formed between modular upstream shell sections 60.

The modular upstream shell sections 60 may be assembled to form at least a portion of the upstream chamber 14. The modular upstream shell sections 60 may form all or substantially all of the upstream chamber 14. For example, the upstream chambers 14 in the example of FIG. 2 and in the example of FIG. 3 are composed essentially of a series of modular upstream shell sections 60 and an upstream end cap 66. The upstream end cap 66 may form a closed end to the upstream chamber 14 and/or may be used to terminate a series of modular upstream shell sections 60.

The modular upstream shell sections 60 may form a hierarchical series, with successive modular upstream shell sections 60 being substantially scaled versions of predecessor modular upstream shell sections 60 (as shown in the example of FIG. 3). Hierarchical modular upstream shell sections 60 generally fit together in a predetermined arrangement with larger modular upstream shell sections 60 coupling to smaller modular upstream shell sections 60. Additionally or alternatively, modular upstream shell sections 60 may by interchangeable and/or nesting. Interchangeable modular upstream shell sections 60 may fit together such that one of several modular upstream shell sections 60 may be used in a location. Nesting modular upstream shell sections 60 may stack compactly together when not assembled in the upstream chamber 14.

The modular upstream shell sections 60 may include one or more section ignition ports 58. Each section ignition port 58 is one of the ignition ports 18 of the upstream chamber 14. Each modular upstream shell section 60 may include at least one section ignition port 58. One or more ignition ports 18 of the upstream chamber 14 may be located in the optional upstream end cap 66. The modular upstream shell sections 60 and/or the upstream end cap 66 may include one or more gas ports 34, one or more sensor ports 74 (as described further herein), and/or one or more pressure relieve devices 68.

Modular upstream shell sections 60 may include coupling structures 106 (such as flanges, shoulders, pins, hooks, threads, etc.) to facilitate mating, assembly, and/or disassembly of modular upstream shell sections 60. Coupling structures 106 and/or modular upstream shell sections 60 may be bolted, snapped, bonded, fastened, or otherwise securely connected together.

As shown in FIGS. 1 and 2, the upstream chamber 14 and/or the modular upstream shell sections 60 may include one or more turbulence structures 64. Each turbulence structure 64 is configured to interfere with laminar flow through the structure such that turbulence in a flowing gas is generally increased by flowing through the turbulence structure 64. The turbulence structure 64 is generally configured to fit within the interior profile 110 of the upstream chamber 14 and may be configured to interfere with gas flowing along the interior walls of the upstream chamber 14. The modular upstream shell sections 60 may be configured to accept the turbulence structure 64 within the interior profile 110 and/or between modular upstream shell sections 60.

The turbulence structure 64 generally blocks a portion of the open area of the interior of the upstream chamber 14. The blocked area tends to induce vortices and turbulence as the flowing gas is redirected into the open areas of the turbulence structure 64 and then expands to the original open area of the upstream chamber 14 after transiting the turbulence structure 64. The blocked portion of the interior area of the upstream chamber 14 may be referred to as the blockage ratio of the turbulence structure 64. The blockage ratio may be a substantial fraction such as at least 10%, at least 20%, at least 40%, or at least 50%. Generally, the turbulence structure 64 has blockage ratio of at most 80% or at most 50%. The turbulence structure 64 typically is configured to withstand the conditions of the combustion front 30 and may be formed of non-flammable materials such as metal and/or ceramic.

Figure 4:
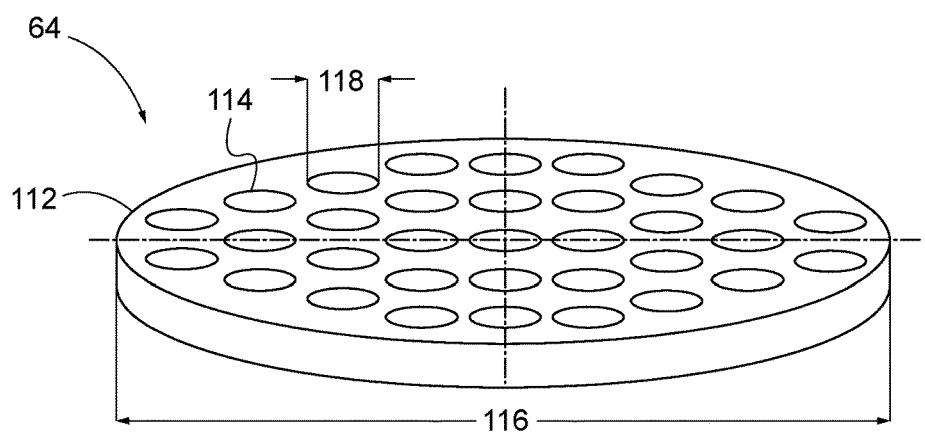
FIG. 4 is a perspective view of an example of a turbulence structure according to the present disclosure.

An example of a turbulence structure 64 is shown in FIG. 4. In FIG. 4, the turbulence structure 64 is an aperture plate 112. The aperture plate 112 is a relatively thin plate with an arrangement of apertures 114. The aperture plate 112 and the apertures 114 are shown as generally circular but other shapes may be used for each or both. The group of apertures 114 may include different shapes and/or sizes. The open area of the aperture plate 112 is the sum of the areas of the apertures 114. The blockage ratio of the aperture plate 112 is ratio of the area not open to the open area of the interior of the corresponding section of the upstream chamber 14 (e.g., the area of the aperture plate 112 as a whole). In the example of FIG. 4 and assuming the turbulence structure 64 is configured to fit snuggly into the upstream chamber 14, the blockage ratio is given by:

$$B_r = 1 - \frac{nd_0^2}{d_1^2} \quad \text{Eq. 2}$$

where $B_r$ is the blockage ratio of the aperture plate 112, n is number of the apertures 114, $d_0$ is the aperture diameter 118, and $d_1$ is the plate diameter 116. Besides the blockage ratio, the number, size, arrangement, and/or shape of the apertures 114 may affect the induced turbulence. Additionally or alternatively, the thickness of the aperture plate 112 and/or the interior profiles of the apertures 114 may affect the induced turbulence. Other examples of turbulence structures 64 include a Shchelkin spiral and a series of annular disks (e.g., a series of aperture plates 112 each with a single, central aperture 114).

Returning to FIGS. 2 and 3, the interior of the downstream chamber 44 may define the divergent duct 72. The divergent duct 72 may direct and/or diffuse the discharged gas 32 from the combustion arrester 20 as the discharged gas 32 propagates through the downstream chamber 44. The divergent duct 72 is a region of the downstream chamber 44 that has an increasing cross sectional area as a function of increasing distance from the upstream end of the divergent duct 72. The upstream end of the divergent duct 72 has a smaller cross sectional area than the downstream end of the divergent duct 72. The upstream end of the divergent duct 72 is at or proximate to the downstream end 24 of the combustion arrester 20. For example, the divergent duct 72 may terminate at the downstream end 24 of the combustion arrester 20. FIG. 3 illustrates a convergent duct 62 or, in alternate (dotted lead lines), a divergent duct 72 of the same general design. In FIGS. 2 and 3, the smaller end 102 of the divergent duct 72 is the upstream end and the larger end 104 of the divergent duct 72 is the downstream end.

As the discharged gas 32 traverses the divergent duct 72 from the combustion arrester 20, the cross sectional area increases and contributes to decreasing the pressure associated with the discharged gas 32. Use of the divergent duct 72 may facilitate a more compact test system 10 and/or may provide for more volume in the downstream chamber 44 for the equivalent length of uniform conduit (not divergent or convergent).

As indicated in the cross sectional view of FIG. 3, the modular downstream shell sections 70 are shells that, together (with or without other components), may form the hollow body of the downstream chamber 44. The interior profiles 110 of the downstream chamber 44 and/or the individual modular downstream shell sections 70 (if present) may be configured as described with respect to the upstream chamber 14 and the modular upstream shell sections 60.

The modular downstream shell sections 70 may be assembled to form at least a portion of the downstream chamber 44. The modular downstream shell sections 70 may form all or substantially all of the downstream chamber 44. For example, the downstream chambers 44 in the example of FIG. 2 and in the example of FIG. 3 are composed essentially of a series of modular downstream shell sections 70 and a downstream end cap 76. The downstream end cap 76 may form a closed end of the downstream chamber 44 and/or may be used to terminate a series of modular downstream shell sections 70.

The modular downstream shell sections 70 may be a series of sections that are interchangeable, hierarchical, and/or nesting. Modular downstream shell sections 70 may include coupling structures 106 as described with respect to modular upstream shell sections 60. Though the modular downstream shell sections 70 may be identical or of the same design as modular upstream shell sections 60, the modular downstream shell sections 70 may be different and not interchangeable with the modular upstream shell sections 60.

Returning to FIG. 1, the test system 10 includes a sensor system 50 with a sensed volume 52 at the downstream end 24 of the combustion arrester 20. The sensor system 50 is configured to measure one or more of the gas composition of the discharged gas 32, the temperature of the discharged gas 32, the pressure in the downstream volume 42, and/or velocity of the discharged gas 32. The sensor system 50 may include one or more sensors for different modalities. Additionally or alternatively, the test system 10 may include one or more sensor systems 50. Sensor systems 50 may be configured to measure the flammable gas 28 and/or the combustion front 30 in the upstream volume 12 and/or to measure the flammable gas 28 in the downstream volume 42.

The sensor system 50 may include a gas composition detection system 82, a temperature sensor 84, a pressure sensor 86, and/or a gas velocity detection system 88. Sensors of the sensor system 50 may be intrusive to the discharged gas 32, potentially affecting the flow of the discharged gas 32, or may be non-intrusive to the discharged gas 32, not disturbing the flow of the discharged gas 32. Intrusive sensors may be simple and reliable to implement but may affect the performance of the combustion arrester 20. Non-intrusive sensors may be more complex and/or indirectly measure flow conditions of the discharged gas 32 but will not affect the performance of the combustion arrester 20. Types of non-intrusive sensors include optical based sensors and gas sampling sensors (provided the gas sample is sufficiently small).

The downstream chamber 44 and/or at least one of the modular downstream shell sections 70 include at least one sensor port 74. The sensor port 74 is configured to accept a sensor of the sensor system 50 and/or to permit access to the discharged gas 32 by the sensor system 50. The sensor port 74 for an optical sensor may be a transparent window (or open aperture) to permit light to be transmitted into and/or out of the downstream chamber 44. The sensor port 74 for a gas sampling sensor may be a gas conduit. The sensor port 74 for a sensor may accommodate power and/or control cabling. Some sensor types may not need a sensor port 74 and may communicate collected data after the combustion arrester test and/or may communicate wirelessly through the downstream chamber 44.

The sensor system 50 may include, and/or may be, optical sensor components such as an optical spectrometer (that may measure absorbance, transmittance, reflectance, scattering, spectrum, luminescence, fluorescence, and/or phosphorescence), a laser-induced fluorescence (LIF) apparatus, a planar laser-induced fluorescence (PLIF) apparatus, a laser-excited atomic fluorescence (LEAF) apparatus, and a Fourier transform infrared (FTIR) spectrometer.

Figure 5:
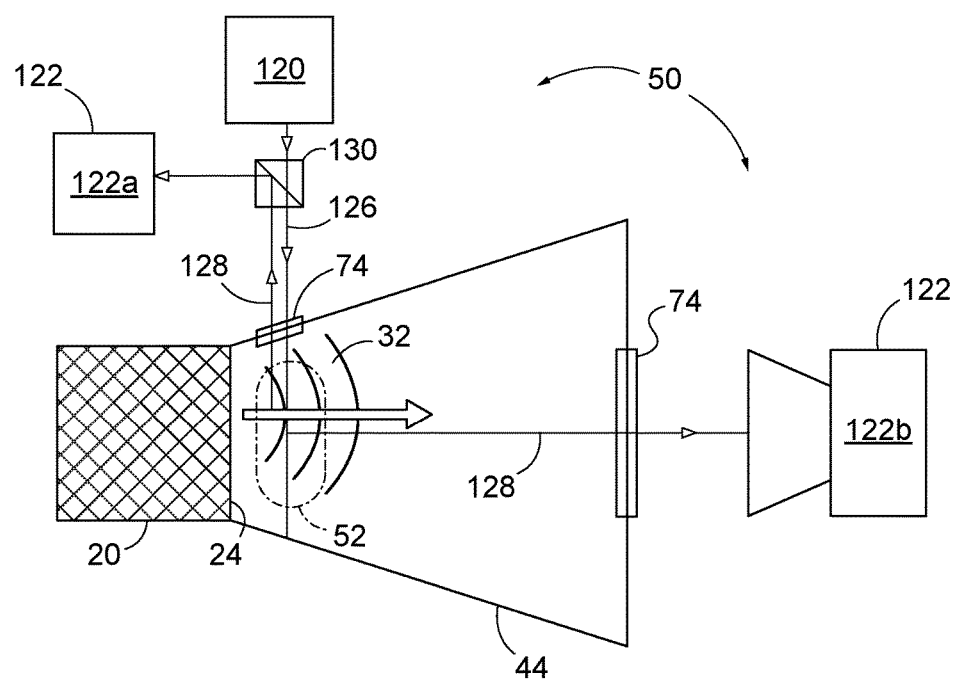
FIG. 5 is a schematic representation of examples of optical sensor system configurations according to the present disclosure.
Figure 6:
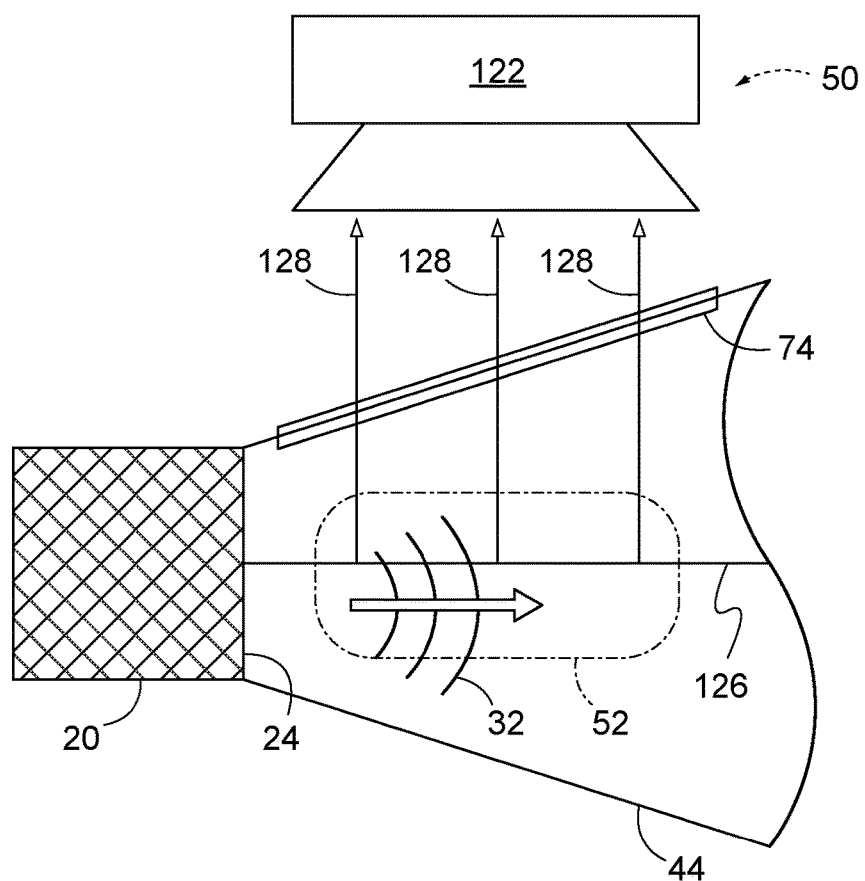
FIG. 6 is a schematic representation of another example of an optical sensor system configuration according to the present disclosure.

As shown in FIGS. 5 and 6, optical sensor components (e.g., the optical spectrometer, the LIF apparatus, the PLIF apparatus, the LEAF apparatus, or the FTIR spectrometer) may be configured to sample and measure a portion (or the entirety) of the discharged gas 32 in a sensed volume 52 that is proximate to the downstream end 24 of the combustion arrester 20. The sensor system 50 may include one or more optical components within the downstream chamber 44 (as shown in FIG. 1) and may include one or more components outside of the sensed volume 52 and/or the downstream chamber 44 (as shown in FIGS. 1, 5, and 6). Generally, the optical sensor components are configured to be non-intrusive and non-disruptive of the discharged gas 32 that is discharged from the downstream end 24 of the combustion arrester 20. For optical components located outside of the downstream chamber 44, those components may be in optical communication with the discharged gas 32 and/or the flammable gas 28 in the downstream volume 42 via one or more sensor ports 74.

The sensor system 50 may include a light source 120 and an optical detector 122. The light source 120 is configured to interrogate the discharged gas 32 and/or the flammable gas 28 in the downstream chamber 44 with an input light beam 126. The light source 120 may include, and/or may be, a laser, a lamp, or an LED (light emitting diode). The light source 120 may generate and/or the input light beam 126 may include light with a wavelength in the ultraviolet (UV), visible, infrared (IR), and/or far infrared (FIR). For example, the light may have a wavelength greater than 100 nm (nanometers), 200 nm, greater than 400 nm, greater than 600 nm, greater than 800 nm, greater than 2,000 nm, greater than 10,000 nm, less than 20,000 nm, less than 4,000 nm, less than 1,000 nm, less than 800 nm, less than 400 nm, and/or less than 300 nm.

The input light beam 126 may be a narrow, line-like beam or may be scanned and/or projected as an extended plane of light (i.e., a light sheet) or as an extended volume of light in the downstream volume 42. For example, the light source 120 may emit a light beam (e.g., a laser beam) that is swept through the downstream volume 42 in a linear manner to illuminate a plane through the downstream volume 42. The plane may be transverse (i.e., transverse to the upstream-downstream direction, as shown in the arrangement of FIG. 5), longitudinal (i.e., parallel to the upstream-downstream direction, as shown in the arrangement of FIG. 6), or skew (i.e., at an angle other than parallel or perpendicular to the upstream-downstream direction). By illuminating a sheet of light, the sensor system 50 may be configured to measure the optical properties of the discharged gas 32 over an extended region (within the sensed volume 52). By measuring the optical properties over the extended region, spatially-resolved properties may be determined. For example, a light sheet illumination may be used to determine a profile of an optical parameter in a cross section of the downstream chamber 44 (e.g., a cross section transverse to the flow of the discharged gas 32, as shown in FIG. 5, or a cross section parallel to the flow of the discharged gas 32, as shown in FIG. 6).

The optical detector 122 is configured to detect output light 128 from the discharged gas 32 due to interaction with the input light beam 126. For example, the output light 128 may be due to scattering (e.g., Rayleigh or Raman scattering) and/or optical emission (e.g., luminescence, fluorescence, and/or phosphorescence emission). The optical detector 122 may include, and/or may be, a camera, a focal plane array, a photodiode, a pyrometer, and/or a photomultiplier tube. The optical detector 122 may be sensitive to light, and the output light 128 may have a wavelength in the ultraviolet, visible, infrared, and/or far infrared. For example, the light may have a wavelength greater than 100 nm, greater than 200 nm, greater than 400 nm, greater than 600 nm, greater than 800 nm, greater than 2,000 nm, greater than 10,000 nm, less than 20,000 nm, less than 4,000 nm, less than 1,000 nm, less than 800 nm, less than 400 nm, and/or less than 300 nm. The optical detector 122 may be configured to detect the light of the input light beam 126 (e.g., for transmission, absorbance, reflection, and scattering (nephelometry) measurements) and/or to reject the light of the input light beam 126 (e.g., for luminescence, fluorescence, phosphorescence, and Raman scattering measurements).

The sensor system 50 may be configured to determine transmission, reflection, absorption, scattering, luminescence, fluorescence, and/or phosphorescence of the discharged gas 32 and/or the flammable gas 28. In scattering, fluorescence, or phosphorescence mode, the sensor system 50 generally has the light source 120 and the optical detector 122 arranged to avoid direct reception of light from the light source 120 by the optical detector 122. For example, and as seen in the examples of FIGS. 5 and 6, the input light beam 126 travels in a different direction than the output light 128. In FIG. 5, the optical detector 122a receives the output light 128 that travels a common path with the input light beam 126 within the sensed volume 52 and is separated by an optical filter 130 (e.g., a dichroic beamsplitter). Such an arrangement may be referred to as an epi-arrangement. In FIG. 5, the optical detector 122b receives the output light 128 that travels substantially orthogonally with respect to the input light beam 126. In both instances shown in FIG. 5, the input light beam 126 interrogates a sensed volume 52 that is substantially transverse to the average flow of the discharged gas 32. In FIG. 6, the optical detector 122 receives the output light 128 that travels substantially orthogonally with respect to the input light beam 126. The light source 120 (not shown in FIG. 6) may be at the downstream end of the downstream chamber 44 or may be in a plane above or below the plane of the drawing. In FIG. 6, the input light beam 126 interrogates a sensed volume 52 that is substantially parallel to the average flow of the discharged gas 32.

In transmission mode (e.g., for transmission or absorbance measurements), the sensor system 50 is arranged such that the discharged gas 32 and/or the flammable gas 28 is optically between the light source 120 and the optical detector 122. For example, the light source 120 and the optical detector 122 may be on opposite sides of the downstream chamber 44. In this arrangement, the optical detector 122 is configured to detect the input light beam 126 that is transmitted through the discharged gas 32 and/or the flammable gas 28. The input light beam 126 is transformed by interaction with the discharged gas 32 and/or the flammable gas 28 into the output light 128 in the form of a transmitted beam and/or an attenuated beam.

A LIF apparatus, a PLIF apparatus, and a LEAF apparatus are analytical apparatuses configured to illuminate a sample containing an indicator species (a molecule or atom) with laser light (the input light beam 126) tuned to excite fluorescence in the indicator species. The fluorescence emission (the output light 128) is detected by the optical detector 122 that is configured to detect light of the fluorescence emission and reject light of the input light beam 126. The spectra, intensity, and lifetime of the fluorescence emission may provide sensitive discrimination of the indicator species over other background species and/or may provide information about the state of the indicator species and/or the local environment near the indicator species. In a PLIF apparatus, the laser light is scanned and/or spread into a light sheet and the fluorescence emission may be detected by an imaging detector.

A FTIR spectrometer is an analytical instrument that measures the infrared absorption or emission spectrum of a sample. The FTIR spectrometer simultaneously collects high spectral resolution data over a wide spectral range. The high spectral resolution and wide spectral range may provide sensitive discrimination of different indicator species in the sample.

Returning generally to FIG. 1, the gas composition detection system 82 of the sensor system 50 is configured to measure the composition of gas in the sensed volume 52. The composition of gas may be the amount and/or presence of one or more chemical components of the gas. The gas in the sensed volume 52 may be the discharged gas 32, the combustion front 30, and/or the flammable gas 28 (e.g., before ignition in the upstream volume 12, before displacement by the discharged gas 32 in the downstream volume 42, and/or after the discharged gas 32 interacts with the flammable gas 28 in the downstream volume 42). Quantities that may be measured by the gas composition detection system 82 may be, and/or may be related to, a concentration, a partial pressure, a molar quantity (e.g., number of moles), a mass, and/or a relative amount.

The gas composition detection system 82 may be configured to detect one or more specific chemical constituents of the gas in the sensed volume 52. For example, the gas composition detection system 82 may be configured to detect a constituent of the flammable gas 28 (such as the combustion fuel, the combustion oxidant, and/or diluents) and/or a combustion product of the flammable gas 28. Detected chemical constituents may be transient or stable combustion species. For example, during combustion reaction, hydroxyl radicals (OH$^-$) and/or other ionic species may be generated. The ionic species typically are short lived, transient products of the combustion species as the ionic species rapidly react to form other compounds. For example, hydroxyl radicals react to form water. Stable combustion species may be reaction end products that do not generally undergo further reaction. Detected chemical constituents (which may be transient or stable) may be partial and/or complete combustion products such as a hydroxyl radical, water, carbon dioxide, carbon monoxide, formaldehyde, nitrogen oxides, hydrogen, and/or methanol. The sensing system 50 may include different gas composition detection systems 82 to detect different chemical constituents. For example, the sensing system 50 may have a rapid detection gas composition detection system 82 to detect one or more transient combustion species and a sensitive gas composition detection system 82 to detect one or more stable combustion species.

The gas composition detection system 82 may be configured to measure a time course of the composition of gas in the sensed volume 52. For example, the gas composition detection system 82 may be configured to repeatedly sample/sense the sensed volume 52 at different points in time to detect the amount and/or presence of one or more chemical components of the gas as a function of time. The gas composition detection system 82 may be configured to measure spatially-resolved compositions of gas in the sensed volume 52. For example, the gas composition detection system 82 may be configured to sample/sense the sensed volume 52 at different spatial locations to detect the amount and/or presence of the one or more chemical components of the gas as a function of position within the sensed volume 52. The spatially-resolved measurements may be three-dimensionally resolved. The spatially-resolved measurements may be a cross sectional profile (generally a two-dimensional profile) of the downstream volume 42 as discussed with respect to FIGS. 5 and 6. The spatially-resolved measurements may be a two-dimensional projection of three-dimensional data (e.g., an integration of values along a line of the input light beam 126).

The gas composition detection system 82 may include, and/or may be, optical sensor components such as described with respect to the sensor system 50 as a whole. For example, the gas composition detection system 82 may include a PLIF apparatus that is configured to remotely measure the concentration of one or more specific species along a plane produced with the input light beam 126. Optical sensor components may be non-intrusive to the discharged gas 32 and/or may be configured to sense with a high time resolution and/or to sense transient combustion species. For example, a PLIF apparatus may be configured to measure hydroxyl radicals in the discharged gas 32 (which may indicate active combustion in the discharged gas 32 or near the downstream end 24 of the combustion arrester 20). Additionally or alternatively, a PLIF apparatus may be configured to measure complete combustion products in the discharged gas 32.

The gas composition detection system 82 may include, and/or may be, a gas analysis component such as a mass spectrometer, a gas chromatograph, or a gas chromatography mass spectrometer. The gas analysis component is a gas sampling device and may be configured to sample a portion (or the entirety) of the discharged gas 32 that is discharged from the downstream end 24 of the combustion arrester 20. The gas analysis component may sample the gas via the sensor port 74, in which case the sensor port 74 includes an orifice or sampling tube to fluidically connect the gas analysis component to the downstream volume 42. The gas analysis component and/or the sensor port 74 may be associated with a sampling valve that is configured to collect aliquots of the discharged gas 32 and/or the flammable gas 28.

A mass spectrometer is an analytical instrument that analyzes a sample by ionizing chemical species in the sample and subjecting the ionized species to electric and magnetic fields to identify mass to charge ratios of the ionized species. The ionized species typically are fragments of the molecular species of the sample. The chemical species may be identified by the mass to charge ratios and/or the pattern of ionized fragments.

A gas chromatograph is an analytical instrument that separates and/or analyzes gaseous and/or vaporous chemical species in a sample (and/or derived from a sample). Gas chromatographs typically detect the retention time of the chemical species travelling through a column.

A gas chromatography mass spectrometer includes a gas chromatograph column input stage and a mass spectrometer detection stage. The gas chromatograph input provides separation of components of the sample prior to mass spectrometry such that gas components may be more specifically determined (e.g., by retention time and mass to charge ratio) than with an ordinary gas chromatograph (e.g., by retention time) or an ordinary mass spectrometer (e.g., by mass to charge ratio).

The gas analysis component (e.g., a mass spectrometer, a gas chromatograph, or a gas chromatography mass spectrometer) may be highly sensitive, detecting very small fractions and/or fractional changes in gas composition. For example, the gas analysis component may detect nanomoles ($10^{-9}$ moles) of specific gas components. The gas analysis component may be configured to measure stable combustion species with high sensitivity. For example, nitric oxide, hydrogen, and methanol in the discharged gas 32 may indicate sufficient energy in the discharged gas 32 to cause ignition of the flammable gas 28 in the downstream volume 42.

The gas composition detection system 82 may combine different types of detection components and these detection components may be configured to measure the same or complementary gas constituents. For example, the gas composition detection system 82 may include an optical sensor component and a gas analysis component. The optical sensor component may be a PLIF apparatus configured to measure transient combustion species (e.g., hydroxyl radicals) and the gas analysis component may be a gas chromatograph configured to measure stable combustion species (e.g., nitric oxide, hydrogen, and/or methanol).

The temperature sensor 84 of the sensor system 50 is configured to measure a temperature of the discharged gas 32. The temperature sensor 84 may include, and/or may be, point measurement device such as a thermocouple or an infrared thermometer. The temperature sensor 84 may be configured to measure temperature across a surface, plane, and/or volume. For example, the temperature sensor 84 may include, and/or may be, a coherent anti-Stokes Raman spectroscopy (CARS) apparatus. CARS is an optical technique to remotely measure gas temperature at a specific location (optionally a spatially-resolved set of locations). CARS uses a nonlinear optical process to determine the vibrational state of a selected chemical species. The temperature of the discharged gas 32 as it exits from the downstream end 24 of the combustion arrester 20 may be related to the quenching performed by the combustion arrester 20 and/or the efficacy of the combustion arrester 20.

The temperature sensor 84 may be configured to measure a time course of the temperature and/or to measure a spatially-resolved temperature in the sensed volume 52. For example, the temperature sensor 84 may be configured to sense the sensed volume 52 at different spatial locations to detect the temperature as a function of position within the sensed volume 52. The spatially-resolved measurements may be three-dimensionally resolved, a cross sectional profile (e.g., a two-dimensional profile), and/or a two-dimensional projection.

The pressure sensor 86 of the sensor system 50 is configured to measure a gas pressure in the downstream volume 42 (i.e., within the downstream chamber 44). The pressure sensor 86 may include, and/or may be, a pressure transducer, a strain gauge, a switch, and/or an optical sensor (e.g., a fiber Bragg grating sensor). The pressure of the discharged gas 32 and/or the pressure differential caused by the discharged gas 32 may be related to the quenching performed by the combustion arrester 20 and/or the efficacy of the combustion arrester 20. The pressure sensor 86 may be a dynamic pressure sensor that is configured to measure a time course of pressure in the downstream chamber 44.

The pressure sensor 86 may include, and/or may be, a threshold sensor and/or indicator. For example, a burst diaphragm may be configured to rupture at a threshold pressure which corresponds to the binary result of whether combustion in the downstream chamber 44 occurred. The burst diaphragm may be configured to withstand pressure from a quenched combustion front 30 that passes through the combustion arrester 20 (i.e., the discharged gas 32 when the combustion arrester 20 sufficiently quenches the combustion front 30 such that the flammable gas 28 in the downstream volume 42 does not ignite). The burst diaphragm may be at the downstream end of the downstream chamber 44 (e.g., in the downstream end cap 76 of the downstream chamber 44). The burst diaphragm may be situated in the central gas flow of gas discharged from the combustion arrester 20 within the downstream chamber 44 or at the downstream end of the downstream chamber 44. The pressure relief device 78 may serve as a pressure sensor 86 as well as relieving excess pressure in the downstream chamber 44.

The gas velocity detection system 88 of the sensor system 50 is configured to measure a velocity (or speed) of the discharged gas 32. For example, the gas velocity detection system 88 may include, and/or may be, an anemometer. The gas velocity detection system 88 may be configured to measure spatially-resolved gas velocity and/or a velocity field of the discharged gas 32. For example, the gas velocity detection system 88 may include, and/or may be, a particle image velocimetry (PIV) apparatus. PIV is an optical technique to remotely measure gas velocity along a defined plane. In PIV, a plane or sheet of light (the input light beam 126) illuminates tracer particles seeded into the gas flow. The observed motion of the tracer particles indicates the spatially-resolved gas flow within the illuminated region. The velocity of the discharged gas 32 may be related to the quenching performed by the combustion arrester 20 and/or the efficacy of the combustion arrester 20.

The sensor system 50 may be configured to detect the presence of ignition and/or a flame in the upstream volume 12 and/or the downstream volume 42. For example, the sensor system 50 may include a flame sensor. Flame sensors typically indicate the presence of a flame by measuring ionic conductivity within the sensed volume 50. Additionally or alternatively, the sensor system 50 may detect the presence of ignition and/or a flame based on heat, pressure and/or gas composition.

The test system 10 may include a controller 90 configured and/or programmed to control the operation of the test system 10 as a whole and/or individual components of the test system 10. The controller 90 may be configured and/or programmed (a) to activate the ignition source 16 to ignite the flammable gas 28 in the upstream volume 12, (b) to measure the presence and/or amount of chemical constituents in the discharged gas 32 and/or the flammable gas 28 with the sensor system 50, (c) to measure fluid and/or physical parameters (e.g., velocity, temperature, and/or pressure) of the discharged gas 32 and/or the flammable gas 28 with the sensor system 50, and/or (d) to quantify performance of the combustion arrester 20 based upon the measured values (such as the presence and/or amount of the chemical constituents in the discharged gas 32 and/or the flammable gas 28, the fluid parameters, and/or the physical parameters). The controller 90 may be configured and/or programmed to operate the gas source 36 to fill the upstream volume 12, the combustion arrester 20, and the downstream volume 42 with the flammable gas 28. The controller 90 may be configured and/or programmed to perform any of the methods described herein. The controller 90 may include a computer, an embedded controller, a programmable logic device, and/or a field-programmable gate array. As used herein, where the controller 90 is configured, adapted, and/or programmed to perform a function, the configuration, adaptation, and/or programming may be in the form of hardware (e.g., wiring, digital logic chips), firmware (e.g., field-programmable gate array, embedded code), and/or software.

As examples of specific controller 90 processes, the controller 90 may be configured and/or programmed to determine a degree of quenching of the combustion front 30 by the combustion arrester 20 and/or an efficacy of the combustion arrester 20. The degree of quenching and/or efficacy may be based on the composition of the discharged gas 32 and/or the physical conditions of the discharged gas 32 (e.g., the temperature, pressure, and/or velocity). For example, the total amount of complete combustion products in the discharged gas 32 may relate to the intensity of combustion in the upstream volume 12 and/or the residence time of combustion within the combustion arrester 20. The presence of transient species in the discharged gas 32 may relate to combustion occurring near the downstream end 24 of the combustion arrester 20. The presence of partial combustion products in the discharged gas 32 may relate to combustion being quickly quenched within the combustion arrester 20.

As further examples of specific controller 90 processes, the controller 90 may be configured and/or programmed to determine a reaction rate within the discharged gas 32 and/or a reaction rate of combustion within the combustion arrester 20. The reaction rates may be based on the composition of the discharged gas 32 and/or the physical conditions of the discharged gas 32 (e.g., the temperature, pressure, and/or velocity). Moreover, the controller 90 may be configured and/or programmed to determine the presence of a flame (e.g., at the downstream end 24 and/or at the upstream end 22 of the combustion arrester 20) based on the composition of the discharged gas 32. The presence of a flame may be determined by determining a prevalence of combustion species (e.g., a lack of combustion reactants and/or an abundance of combustion products) and/or by determining conditions indicative of or conducive to combustion (e.g., ionic species, temperature, pressure, and/or velocity).

Figure 7:
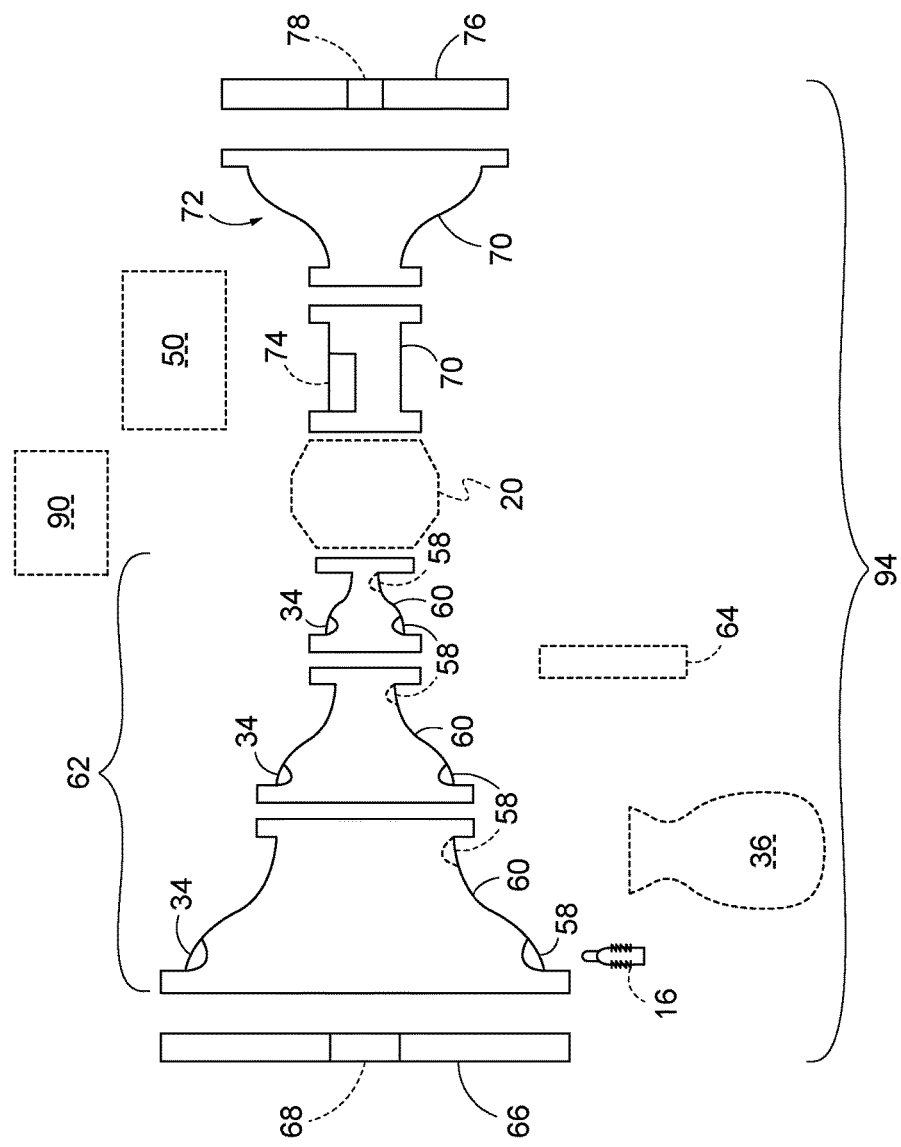
FIG. 7 is a schematic representation of an example of a test kit for combustion arrester testing according to the present disclosure.

As schematically represented in FIG. 7, the test system 10 may be assembled and/or reconfigured from a kit 94 of the components. The kit 94 includes a hierarchical series of modular upstream shell sections 60 and a series of modular downstream shell sections 70. The hierarchical series of modular upstream shell sections 60 are configured to produce the convergent duct 62 (e.g., at least one of the modular upstream shell sections 60 has the form of the convergent duct 62). The series of modular downstream shell sections 70 may be a hierarchical series of modular downstream shell sections 70 and/or may be configured to produce the divergent duct 72 (e.g., at least one of the modular downstream shell sections 70 has the form of the divergent duct 72). The kit 94 may include the upstream end cap 66 and/or the downstream end cap 76. The modular upstream shell sections 60 along with the optional upstream end cap 66 may be coupled together in various arrangements to produce the upstream chamber 14. Different upstream chamber 14 configurations may be achieved by using more or less modular upstream shell sections 60 and/or by arranging the modular upstream shell sections 60 in different orders. The modular downstream shell sections 70 along with the optional downstream end cap 76 may be coupled together in various arrangements to produce the downstream chamber 44. Different downstream chamber 44 configurations may be achieved by using more or less modular downstream shell sections 70 and/or by arranging the modular downstream shell sections 70 in different orders.

The kit 94 may include the turbulence structure 64, the ignition source 16, the gas source 36, the sensor system 50, and/or the controller 90. The turbulence structure 64 is configured to fit within the upstream chamber 14 (e.g., within the interior profile 110 of the upstream chamber 14 and/or between modular upstream shell sections 60. The ignition source 16 is configured to fit into at least one of the section ignition ports 58. Typically, the ignition source 16 may fit in any of the section ignition ports 58.

Figure 8:
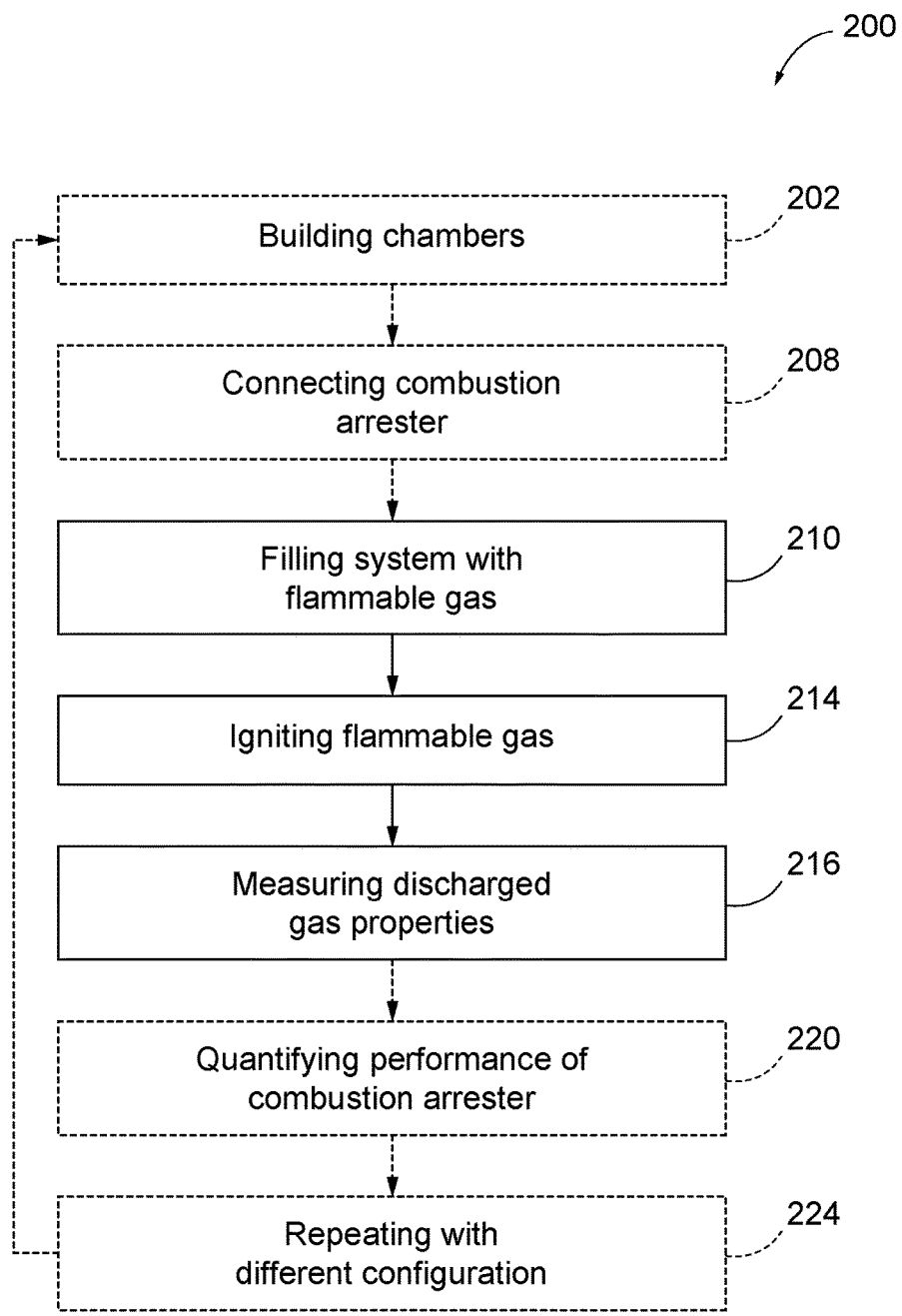
FIG. 8 is a schematic representation of methods of combustion arrester testing according to the present disclosure.

FIG. 8 schematically represents methods 200 of testing combustion arresters (such as combustion arresters 20). Methods 200 include filling 210 the test system (e.g., test system 10) with flammable gas (e.g., flammable gas 28), igniting 214 the flammable gas, and measuring 216 properties of gas discharged due to the ignition (e.g., discharged gas 32). Prior to filling 210 and/or igniting 214, methods 200 may include building 202 upstream and downstream chambers (e.g., upstream chamber 14 and downstream chamber 44) to fill with the flammable gas and/or may include connecting 208 the combustion arrester to the upstream and downstream chambers. After igniting 214 and/or measuring 216, methods 200 may include quantifying 220 the performance of the combustion arrester and/or may include repeating 224 the testing with a different configuration.

For example, methods 200, which may be referred to as methods of quantifying combustion arrester performance, may include filling 210 an upstream volume (e.g., upstream volume 12) and the combustion arrester with flammable gas, igniting 214 the flammable gas in the upstream volume (upstream of the combustion arrester), measuring 216 the composition of gas discharged from the combustion arrester (downstream of the combustion arrester and due to igniting 214), and quantifying 220 the performance of the combustion arrester based on the composition of gas measured. As another example, methods 200, which may be referred to as methods of testing combustion arresters, may include building 202 upstream and downstream chambers in a manner to define a convergent duct (e.g., convergent duct 62) in the upstream chamber, connecting 208 the combustion arrester to the upstream and downstream chambers, filling 210 the upstream chamber, the combustion arrester, and the downstream chamber with the flammable gas, igniting 214 the flammable gas in the upstream chamber, and measuring 216 whether the flammable gas in the downstream chamber ignited in response to igniting 214 the flammable gas in the upstream chamber.

Generally, methods 200 include simulating and/or reproducing combustion conditions expected when the combustion arrester is deployed. Further, methods 200 may include simulating and/or reproducing predefined combustion conditions, such as combustion conditions selected to sample expected conditions during deployment (of the combustion arrester) and/or worst-case conditions. Parameters that affect combustion arrester performance and/or efficacy include:

(a) the flammable gas,
(b) the temperature of the combustion arrester,
(c) the pressure and temperature of the flammable gas when the combustion front (e.g., combustion front 30) enters the combustion arrester,
(d) the gas flow across the combustion arrester (e.g., from the upstream end 22 to the downstream end 24),
(e) the propagation velocity of the combustion front, and
(f) the volume of burned gases that will flow through the combustion arrester.

In particular, the parameters (c), (d), (e), and (f) are strongly dependent on the geometry of the upstream chamber and the downstream chamber. For example, the upstream volume, the downstream volume, the character of the combustion front (e.g., a deflagration or detonation; laminar flow or turbulent flow), and the location of the ignition source (e.g., ignition source 16) within the upstream volume and with respect to the combustion arrester each may affect the parameters (c), (d), (e), and (f). The size and/or internal design of the combustion arrester also may strong affect the parameters (c), (d), (e), and (f). Parameter (a), the flammable gas, includes the types of flammable gas components (e.g., the combustion fuel, combustion oxidant, and diluent, if any) and the relative abundances of the flammable gas components (e.g., the equivalence ratio). Different flammable gases may burn with different intensities, may produce different combustion reaction products, may have different heat capacities, and/or may have different viscosities. Parameter (b), the temperature of the combustion arrester, may affect the combustion arrester performance because the quenching of the combustion front is typically due to substantial cooling of the burning gases to a temperature below the autoignition temperature.

Building 202 the upstream and downstream chambers generally includes assembling the upstream chamber and assembling the downstream chamber. The upstream chamber and the downstream chamber may each be assembled of modular shell sections and/or end caps such as modular upstream shell sections 60, upstream end cap 66, modular downstream shell sections 70, and/or downstream end cap 76. Assembling each of the chambers may include selecting the number and/or type of modular shell sections to produce the desired volume for the respective chamber (e.g., the upstream volume 12 for the upstream chamber 14 and the downstream volume 42 for the downstream chamber 44). Further, assembling the upstream chamber and/or assembling the downstream chamber may include defining a corresponding closed volume that may facilitate filling 210 and/or containing the flammable gas before ignition. As discussed with respect to the upstream chamber 14 and the downstream chamber 44, the respective closed volumes may be configured to rupture or otherwise become open volumes after ignition or after sufficiently intense ignition. Open volumes (whether before or after ignition) may simulate very large upstream volumes or downstream volumes (potentially such volumes may be treated as infinite).

Assembling the upstream chamber and assembling the downstream chamber may include selecting a volume ratio of the upstream chamber to the downstream chamber. The selected volumes and/or volume ratio may be selected to simulate and/or reproduce combustion conditions expected when the combustion arrester is deployed. Additionally or alternatively, the volumes and/or volume ratio may be selected to simulate and/or reproduce predefined combustion conditions, such as combustion conditions selected to sample expected conditions during deployment and/or worst-case conditions. Control of the volumes and/or volume ratio may affect parameters (c), (d), (e), and, in particular, (f). For example, the length of time the combustion arrester is exposed to the hot, burning gas of the combustion front may be affected by the selected volumes and/or volume ratio.

Building 202 the upstream and downstream chambers may include forming the convergent duct in the upstream chamber and/or forming a divergent duct (e.g., the divergent duct 72) in the downstream chamber. The convergent duct may be defined by one or more modular upstream shell sections. Generally, the convergent duct terminates at the downstream end of the upstream chamber (and where the upstream chamber is connected to the combustion arrester). The divergent duct may be defined by one or more modular downstream shell sections. Generally, the divergent duct terminates at the upstream end of the downstream chamber (and where the downstream chamber is connected to the combustion arrester). Control of the convergent duct in terms of placement, taper, length, and/or interior profile (e.g., the interior profile 110) may affect parameters (c), (d), (e), and (f).

Methods 200 generally, and building 202 specifically, may include installing the ignition source at a location along the upstream chamber. The ignition source may be installed in an ignition port (e.g., the ignition port 18, the section ignition port 58). If the upstream chamber includes more than one ignition port, unused ignition ports may be sealed and/or may have alternate ignition sources installed. The ignition source (or one of the ignition sources) may be used to ignited the flammable gas, i.e., by igniting 214). The type of ignition source (e.g., electrical or explosive), energy released by the ignition source, and/or location of the ignition source may be selected to simulate and/or reproduce combustion conditions expected when the combustion arrester is deployed. Additionally or alternatively, the type, energy, and/or location of the ignition source may be selected to simulate and/or reproduce predefined combustion conditions, such as combustion conditions selected to sample expected conditions during deployment and/or worst-case conditions. Control of the type, energy, and/or location of the ignition source may affect parameter (f) and, in particular, parameters (c), (d), and (e). For example, the flame speed of the combustion front impinging the combustion arrester may be controlled by the selected type, energy, and/or location of the ignition source. The flame speed affects the length of time the combustion arrester is exposed to the hot, burning gas of the combustion front.

Methods 200 generally, and building 202 specifically, may include installing a turbulence structure (e.g., turbulence structure 64) in the upstream chamber. The turbulence structure may be used to affect the flow conditions of the combustion front (e.g., the flame velocity and the amount of turbulence). Control of the turbulence may affect parameters (c), (d), (e), and (f).

Connecting 208 the combustion arrester to the upstream and downstream chambers may include fluidically connecting the upstream chamber to the downstream chamber via the combustion arrester. The downstream end of the upstream chamber is connected to the upstream end of the combustion arrester. The downstream end of the combustion arrester is connected to the upstream end of the downstream chamber.

Filling 210 the test system with flammable gas may include sealing the upstream chamber and/or the downstream chamber. Additionally or alternatively, filling 210 with flammable gas may include flowing the flammable gas through the upstream chamber, the combustion arrester, and/or the downstream chamber. Filling 210 with flammable gas may include introducing the flammable gas into the upstream chamber (and/or the downstream chamber) via a gas port (e.g., gas port 34). The flammable gas may be filled from a gas source (e.g., gas source 36). The flammable gas may be mixed from components (e.g., the combustion fuel, the combustion oxidant, and/or the diluent) before and/or after introducing the components into the test system. Filling 210 may include equalizing pressure of the flammable gas between the upstream chamber, the combustion arrester, and the downstream chamber (before igniting 214 the flammable gas). Filling 210 may include equalizing temperature of the flammable gas, the upstream chamber, the combustion arrester, and the downstream chamber (before igniting 214 the flammable gas). Equalizing the pressure and/or the temperature may produce more consistent results than if ignition occurs before equalizing. Alternatively, the pressure and/or temperature of one or more components may be controlled independently (e.g., a temperature gradient from the upstream chamber to the downstream chamber).

Igniting 214 the flammable gas is performed in the upstream chamber (or the upstream volume). Ignition may be initiated by activating the ignition source. The ignition causes the combustion front to propagate toward the combustion arrester. As discussed, the location of ignition, the character (e.g., spark, heat, or explosion), and the energy released by the ignition source may affect the propagation of the combustion front.

Measuring 216 the discharged gas properties may include measuring chemical properties (e.g., the composition of the discharged gas) and/or physical properties (e.g., temperature, pressure, and/or velocity of the discharged gas). Measuring 216 may include measuring quantitative and/or qualitative parameters relating to the discharged gas and/or the effectiveness of the combustion arrester (such as whether the flammable gas in the downstream chamber ignited in response to igniting 214 the flammable gas in the upstream chamber). Generally, measuring 216 includes measuring the discharged gas properties in a sensed volume (e.g., the sensed volume 52) that is proximate and/or adjacent to the downstream end of the combustion arrester. Measuring 216 may include using a sensor system such as sensor system 50.

Measuring 216 may include measuring a property at defined moment in time, averaging or integrating the property for a period of time, measuring the property as a function of time (a time course), and/or performing spatially resolved measurements of the property. Spatially resolved properties may be three-dimensionally resolved, a cross sectional profile of the downstream volume (or upstream volume), and/or a two-dimensional projection.

Measuring 216 may include measuring by disturbing the discharged gas flow (intrusive measurement) or without significantly interfering with the discharged gas flow (non-intrusive measurement). Examples of non-intrusive measurements include optical detection (e.g., measuring 216 by optically interrogating the discharged gas. in the sensed volume. Gas sampling and small sensor probes may cause little disturbance of the discharged gas flow. Non-intrusive measurements facilitate observation of the dynamics of the discharged gas (and the performance of the combustion arrester) without affecting the measurement.

Measuring the composition of the discharged gas may include measuring a quantity related to an amount of a combustion species in the discharged gas. More than one combustion species may be measured. Combustion species include components of the flammable gas (combustion reactants and diluents) and combustion products of the flammable gas. Quantities measured may be concentration, partial pressure, molar quantities (e.g., number of moles), mass, and/or relative amounts. Measuring 216 may include measuring one or more transient combustion species and/or one or more stable combustion species. Measuring 216 may include measuring one or more partial combustion products and/or one or more complete combustion products. Combustion species for measurement may be selected from hydroxyl radical, water, carbon dioxide, carbon monoxide, formaldehyde, nitric oxide, nitrous oxide, hydrogen, methanol, a hydrocarbon fuel, and other specific combustion species according to the composition of the flammable gas.

Measuring the composition of gas may include measuring by planar laser-induced fluorescence, laser-induced fluorescence, laser-excited atomic fluorescence, and/or Fourier transform infrared spectroscopy. Measuring the composition of gas may include measuring by mass spectrometry, gas chromatography, and/or a gas chromatography mass spectrometry.

Measuring physical properties may include measuring the temperature of the discharged gas, e.g., with a thermocouple, an infrared thermometer, or by coherent anti-Stokes Raman spectroscopy. Measuring physical properties may include measuring the velocity of the discharged gas, e.g., with an anemometer or particle image velocimetry. Measuring physical properties may include measuring the pressure of the discharged gas (and/or the flammable gas) in the downstream chamber, e.g., with a pressure transducer, a strain gauge, a switch, and/or an optical sensor.

Quantifying 220 the performance of the combustion arrester may include quantifying the properties measured by measuring 216 and/or generating one or more derivative measures based on the properties measured. For example, the efficacy of the combustion arrester may be related to the composition of the discharged gas (e.g., types and amounts of components), the temperature of the discharged gas, the pressure in the downstream chamber, and/or the velocity of the discharged gas. Derivative measures may include the rate of combustion in the combustion arrester (as indicated by the discharged gas components and the time course of components), the discharged gas temperature relative to the autoignition temperature of the flammable gas, the peak pressure due to the discharged gas, and/or the velocity of the discharged gas relative to the velocity of the combustion front and/or the velocity of sound in the flammable gas.

Repeating 224 the testing with a different configuration may include performing one or more steps of the method 200 (except for repeating 224) with a different configuration. The different configuration may include a differences in the upstream volume, the downstream volume, the volume ratio of the upstream volume to the downstream volume, the shape of the upstream chamber, the shape of the downstream chamber, the presence and/or type of turbulence structure, the ignition source location, the ignition source energy, the ignition source type, the flammable gas, the test system temperature, the flammable gas temperature, and/or the test system pressure. Repeating 224 may be used to sample a set of parameters so that the combustion arrester is tested across the expected conditions where the combustion arrester is deployed and/or under worst-case conditions.

Examples of inventive subject matter according to the present disclosure are described in the following enumerated paragraphs.

A1. A system for quantifying combustion arrester performance, the system comprising:

a combustion arrester having an upstream end and a downstream end;

an ignition source upstream from the combustion arrester;

a sensor system with a sensed volume at the downstream end of the combustion arrester, the sensor system configured to measure a composition of gas discharged from the downstream end of the combustion arrester; and an optional controller configured to quantify performance of the combustion arrester based on the composition of gas measured by the sensor system.

A2. The system of paragraph A1, wherein the sensor system is configured to measure a quantity related to an amount of a combustion species in the gas discharged from the downstream end of the combustion arrester.

A2.1. The system of paragraph A2, wherein the quantity related to an amount is a concentration, a partial pressure, a molar quantity, a mass, or a relative amount.

A2.2. The system of any of paragraphs A2-A2.1, wherein the combustion species is a chemical constituent of a flammable gas in contact with the ignition source or a combustion product of the flammable gas.

A2.3. The system of any of paragraphs A2-A2.2, wherein the combustion species is a transient combustion species or a stable combustion species.

A2.4. The system of any of paragraphs A2-A2.3, wherein the combustion species is a partial combustion product and/or a complete combustion product.

A2.5. The system of any of paragraphs A2-A2.4, wherein the combustion species is one of a hydroxyl radical, water, carbon dioxide, carbon monoxide, formaldehyde, nitric oxide, nitrous oxide, hydrogen, methanol, and a hydrocarbon fuel.

A2.6. The system of any of paragraphs A2-A2.5, wherein the combustion species is a combustion reactant of a flammable gas that is in contact with the ignition source.

A2.7. The system of any of paragraphs A2-A2.6, wherein the sensor system is configured to measure a first quantity related to a first amount of a first combustion species in the gas discharged from the downstream end of the combustion arrester and is configured to measure a second quantity related to a second amount of a second combustion species in the gas discharged from the downstream end of the combustion arrester.

A3. The system of any of paragraphs A1-A2.7, wherein the sensor system is configured to measure a time course of the composition of the gas discharged from the downstream end of the combustion arrester.

A4. The system of any of paragraphs A1-A3, wherein the sensor system is configured to measure a cross-sectional composition profile of the gas discharged from the downstream end of the combustion arrester.

A5. The system of any of paragraphs A1-A4, wherein the sensor system includes a temperature sensor configured to measure a temperature of the gas discharged from the downstream end of the combustion arrester.

A5.1. The system of paragraph A5, wherein the temperature sensor includes a coherent anti-Stokes Raman spectroscopy apparatus configured to measure the temperature of the gas discharged from the downstream end of the combustion arrester.

A5.2. The system of any of paragraphs A5-A5.1, wherein the temperature sensor is configured to measure a cross-sectional temperature profile of the gas discharged from the downstream end of the combustion arrester.

A6. The system of any of paragraphs A1-A5.2, wherein the sensor system is configured to measure a velocity of the gas discharged from the downstream end of the combustion arrester.

A6.1. The system of paragraph A6, wherein the sensor system includes an anemometer configured to measure the velocity of the gas discharged from the downstream end of the combustion arrester.

A6.2. The system of any of paragraphs A6-A6.1, wherein the sensor system includes a particle image velocimetry apparatus configured to measure the velocity of the gas discharged from the downstream end of the combustion arrester.

A6.2.1. The system of paragraph A6.2, wherein the particle image velocimetry apparatus is configured to measure cross-sectional velocity profile of the gas discharged from the downstream end of the combustion arrester.

A7. The system of any of paragraphs A1-A6.2.1, wherein the sensor system includes a pressure sensor configured to measure a pressure of gas in a downstream volume configured to receive the gas discharged from the downstream end of the combustion arrester.

A8. The system of any of paragraphs A1-A7, wherein the sensor system includes an optical sensor component.

A8.1. The system of paragraph A8, wherein the optical sensor component includes at least one of a planar laser-induced fluorescence apparatus, a laser-induced fluorescence apparatus, a laser-excited atomic fluorescence apparatus, an optical spectrometer, and a Fourier transform infrared spectrometer.

A8.2. The system of any of paragraphs A8-A8.1, wherein the optical sensor component includes a coherent anti-Stokes Raman spectroscopy apparatus that is optionally configured to measure a temperature profile of the gas discharged from the downstream end of the combustion arrester.

A8.3. The system of any of paragraphs A8-A8.2, wherein the optical sensor component includes a particle image velocimetry apparatus that is optionally configured to measure a velocity profile of the gas discharged from the downstream end of the combustion arrester.

A9. The system of any of paragraphs A1-A8.3, wherein the sensor system includes at least one of a mass spectrometer, a gas chromatograph, and a gas chromatography mass spectrometer.

A10. The system of any of paragraphs A1-A9, wherein the sensor system is configured to be non-disruptive to gas flow from the combustion arrester from the downstream end of the combustion arrester.

A11. The system of any of paragraphs A1-A10, wherein the sensor system is configured to detect the presence of ignition and/or a flame in the upstream volume and/or the downstream volume.

A12. The system of any of paragraphs A1-A11, further comprising an upstream chamber that defines an upstream volume and encloses the ignition source, the upstream volume being in fluidic contact with the upstream end of the combustion arrester.

A12.1. The system of paragraph A12, wherein the upstream chamber terminates at the upstream end of the combustion arrester.

A12.2. The system of any of paragraphs A12-A12.1, wherein the upstream chamber and the combustion arrester are filled with a flammable gas.

A13. The system of any of paragraphs A1-A12.2, further comprising a downstream chamber that defines a downstream volume that is in fluidic contact with the downstream end of the combustion arrester.

A13.1. The system of paragraph A13, wherein the downstream chamber terminates at the downstream end of the combustion arrester.

A13.2. The system of any of paragraphs A13-A13.1, wherein the downstream volume and the combustion arrester are filled with a flammable gas.

A13.3. The system of any of paragraphs A13-A13.2, wherein the downstream chamber is configured to receive the gas discharged from the downstream end of the combustion arrester.

A14. The system of any of paragraphs A1-A13.3, wherein the controller is configured to operate the sensing system to measure the gas discharged from the combustion arrester at the downstream end.

A15. The system of any of paragraphs A1-A14, wherein the controller is configured to operate the ignition source to ignite a/the flammable gas upstream of the combustion arrester.

A16. The system of any of paragraphs A1-A15, wherein the controller is configured to determine a degree of quenching by the combustion arrester of a combustion front generated upstream of the combustion arrester by the ignition source based upon the composition of the gas discharged from the downstream end of the combustion arrester.

A17. The system of any of paragraphs A1-A16, wherein the controller is configured to determine an efficacy of the combustion arrester based upon the composition of the gas discharged from the downstream end of the combustion arrester.

A18. The system of any of paragraphs A1-A17, wherein the controller is configured to determine a reaction rate of the gas discharged from the downstream end of the combustion arrester and/or to determine a reaction rate of gas in the combustion arrester based on a time course of the composition of the gas discharged from the downstream end of the combustion arrester.

A19. The system of any of paragraphs A1-A18, wherein the controller is configured to determine a presence of a flame at the downstream end of the combustion arrester based on the composition of the gas discharged from the downstream end of the combustion arrester, optionally by determining a prevalence of a/the combustion species in the gas discharged from the downstream end of the combustion arrester.

A20. The system of any of paragraphs A1-A19, wherein the controller is configured to determine a presence of a flame at the upstream end of the combustion arrester based on the composition of the gas discharged from the downstream end of the combustion arrester, optionally by determining a prevalence of a/the combustion in the gas discharged from the downstream end of the combustion arrester.

A21. The system of any of paragraphs A1-A20, wherein the combustion arrester is at least one of a flame arrester, a flame trap, a deflagration arrester, and a detonation arrester.

A22. The system of any of paragraphs A1-A21, wherein the upstream volume and/or the downstream volume, where used, are the respective upstream volume and/or the downstream volume of any of paragraphs C1-C12.2.

A23. The use of any of the systems of paragraphs A1-A22 to determine an effectiveness of the combustion arrester.

B1. A method of quantifying combustion arrester performance, the method comprising:
filling an upstream volume and a combustion arrester with a flammable gas;
igniting the flammable gas in the upstream volume, upstream of the combustion arrester;
measuring a composition of gas discharged from the combustion arrester, downstream of the combustion arrester, after igniting the flammable gas; and
quantifying a performance of the combustion arrester based on the composition of gas measured.

B2. The method of paragraph B1, wherein measuring the composition includes measuring a quantity related to an amount of a combustion species in the gas discharged from the combustion arrester.

B2.1. The method of paragraph B2, wherein the quantity related to an amount is a concentration, a partial pressure, a molar quantity, a mass, or a relative amount.

B2.2. The method of any of paragraphs B2-B2.1, wherein the combustion species is a chemical constituent of the flammable gas and/or a combustion reaction product of the flammable gas.

B2.3. The method of any of paragraphs B2-B2.2, wherein the combustion species is a transient combustion species or a stable combustion species.

B2.4. The method of any of paragraphs B2-B2.3, wherein the combustion species is a partial combustion product and/or a complete combustion product.

B2.5. The method of any of paragraphs B2-B2.4, wherein the combustion species is one of a hydroxyl radical, water, carbon dioxide, carbon monoxide, formaldehyde, nitric oxide, nitrous oxide, hydrogen, methanol, and a hydrocarbon fuel.

B2.6. The method of any of paragraphs B2-B2.5, wherein the combustion species is a combustion reactant of the flammable gas.

B2.7. The method of any of paragraphs B2-B2.6, wherein measuring the composition of gas includes measuring a first quantity related to a first amount of a first combustion species in the gas discharged from the combustion arrester and measuring the composition of gas includes measuring a second quantity related to a second amount of a second combustion species in the gas discharged from the combustion arrester.

B3. The method of any of paragraphs B1-B2.7, wherein measuring the composition includes measuring a time course of the composition of the gas discharged from the combustion arrester.

B4. The method of any of paragraphs B1-B3, wherein measuring the composition includes measuring a cross-sectional composition profile of the gas discharged from the combustion arrester.

B5. The method of any of paragraphs B1-B4, wherein measuring the composition includes measuring the composition of the gas without interfering with gas flow from the combustion arrester.

B6. The method of any of paragraphs B1-B5, wherein measuring the composition includes optically interrogating the gas discharged from the combustion arrester.

B7. The method of any of paragraphs B1-B6, wherein measuring the composition includes measuring the composition of the gas by one or more of planar laser-induced fluorescence, laser-induced fluorescence, laser-excited atomic fluorescence, and Fourier transform infrared spectroscopy.

B8. The method of any of paragraphs B1-B7, wherein measuring the composition includes measuring the composition of the gas by one or more of mass spectrometry, gas chromatography, and gas chromatography mass spectrometry.

B9. The method of any of paragraphs B1-B8, further comprising measuring a temperature of the gas discharged from the combustion arrester and wherein quantifying includes quantifying the performance based on the temperature of the gas discharged from the combustion arrester.

B9.1. The method of paragraph B9, wherein measuring the temperature includes measuring a time course of the temperature of the gas discharged from the combustion arrester.

B9.2. The method of any of paragraphs B9-B9.1, wherein measuring the temperature includes measuring a cross-sectional temperature profile of the gas discharged from the combustion arrester.

B9.3. The method of any of paragraphs B9-B9.2, wherein measuring the temperature includes measuring the temperature without interfering with gas flow from the combustion arrester.

B9.4. The method of any of paragraphs B9-B9.3, wherein measuring the temperature includes optically interrogating the gas discharged from the combustion arrester.

B9.5. The method of any of paragraphs B9-B9.4, wherein measuring the temperature includes measuring the temperature by coherent anti-Stokes Raman spectroscopy.

B10. The method of any of paragraphs B1-B9.5, further comprising measuring a velocity of the gas discharged from the combustion arrester and wherein quantifying includes quantifying the performance based on the velocity of the gas discharged from the combustion arrester.

B10.1. The method of paragraph B10, wherein measuring the velocity includes measuring a time course of the velocity of the gas discharged from the combustion arrester.

B10.2. The method of any of paragraphs B10-B10.1, wherein measuring the velocity includes measuring a cross-sectional velocity profile of the gas discharged from the combustion arrester.

B10.3. The method of any of paragraphs B10-B10.2, wherein measuring the velocity includes measuring the velocity without interfering with gas flow from the combustion arrester.

B10.4. The method of any of paragraphs B10-B10.3, wherein measuring the velocity includes optically interrogating the gas discharged from the combustion arrester.

B10.5. The method of any of paragraphs B10-B10.4, wherein measuring the velocity includes measuring the velocity with an anemometer.

B10.6. The method of any of paragraphs B10-B10.5, wherein measuring the velocity includes measuring the velocity by particle image velocimetry.

B11. The method of any of paragraphs B1-B10.6, further comprising discharging the gas discharged from the combustion arrester into a downstream chamber and measuring a pressure in the downstream chamber due to the gas discharged from the combustion arrester.

B11.1. The method of paragraph B11, wherein measuring the pressure includes measuring a time course of the pressure in the downstream chamber.

B11.2. The method of any of paragraphs B11-B11.1, wherein measuring the pressure includes measuring the pressure without interfering with gas flow from the combustion arrester.

B12. The method of any of paragraphs B1-B11.2, wherein filling the upstream volume includes filling an upstream chamber that defines the upstream volume, the combustion arrester, and a downstream chamber with the flammable gas.

B12.1. The method of paragraph B12, wherein filling the upstream volume includes equalizing pressure of the flammable gas between the upstream chamber, the combustion arrester, and the downstream chamber, before igniting the flammable gas.

B12.2. The method of any of paragraphs B12-B12.1, wherein filling the upstream volume includes equalizing temperature of the flammable gas, the upstream chamber, the combustion arrester, and the downstream chamber, before igniting the flammable gas.

B12.3. The method of any of paragraphs B12-B12.2, wherein the upstream volume is a closed volume of the upstream chamber before igniting the flammable gas.

B12.4. The method of any of paragraphs B12-B12.3, wherein the downstream chamber defines a closed downstream volume before igniting the flammable gas.

C1. A system for testing a combustion arrester, the system comprising:

an upstream chamber that defines an upstream volume and includes an ignition port configured to receive an ignition source;

a downstream chamber that defines a downstream volume; and a combustion arrester between the upstream chamber and the downstream chamber;

wherein the upstream chamber defines a convergent duct that converges toward the combustion arrester and terminates at the combustion arrester.

C2. The system of paragraph C1, further comprising a flammable gas that fills the upstream volume, the downstream volume, and the combustion arrester.

C3. The system of any of paragraphs C1-C2, wherein the upstream chamber includes a hierarchical series of modular upstream shell sections that at least partially define the upstream volume and the convergent duct.

C3.1. The system of paragraph C3, wherein each of the modular upstream shell sections includes a section ignition port configured to receive an ignition source and wherein the ignition port is one of the section ignition ports, and optionally wherein all of the ignition ports of the hierarchical series of modular shell sections are sealed.

C3.2. The system of any of paragraphs C3-C3.1, wherein at least one of the modular upstream shell sections has a gas port configured to transfer gas into the upstream chamber, and optionally wherein each of the modular upstream shell sections has a gas port.

C3.3. The system of any of paragraphs C3-C3.2, wherein the modular upstream shell sections each have an interior profile configured to produce laminar flow and/or top-hat flow of the flammable gas through the convergent duct toward the combustion arrester.

C4. The system of any of paragraphs C1-C3.3, further comprising an ignition source installed in the ignition port.

C4.1. The system of paragraph C4, wherein the ignition source includes, optionally is, an electrical arc source.

C5. The system of any of paragraphs C1-C4.1, wherein the upstream chamber has an interior profile configured to produce laminar flow and/or top-hat flow of the flammable gas through the convergent duct toward the combustion arrester.

C6. The system of any of paragraphs C1-C5, further comprising a turbulence structure in the convergent duct.

C6.1. The system of paragraph C6, wherein the turbulence structure is an aperture plate.

C6.2. The system of any of paragraphs C6-C6.1, wherein the turbulence structure has a blockage ratio of at least 10%, at least 20%, at least 40%, at least 50%, at most 80%, and/or at most 50%.

C7. The system of any of paragraphs C1-C6.2, wherein the downstream chamber includes a series of modular downstream shell sections that at least partially define the downstream volume.

C7.1. The system of paragraph C7, wherein the series of modular downstream shell sections is a hierarchical series of modular downstream shell sections.

C7.2. The system of any of paragraphs C7-C7.1, wherein the modular downstream shell sections each have an interior profile configured to produce laminar flow and/or top-hat flow of the flammable through the downstream chamber and directed away from the combustion arrester.

C8. The system of any of paragraphs C1-C7.2, wherein the downstream chamber defines a divergent duct that diverges away from the combustion arrester and terminates at the combustion arrester.

C9. The system of any of paragraphs C1-C8, wherein the downstream chamber has an interior profile configured to produce laminar flow and/or top-hat flow of the flammable gas through the downstream chamber and directed away from the combustion arrester.

C10. The system of any of paragraphs C1-C9, further comprising a pressure sensor configured to measure a pressure of gas in the downstream chamber.

C10.1. The system of paragraph C10, wherein the pressure sensor is a dynamic pressure sensor configured to measure a time course of pressure in the downstream chamber.

C10.2. The system of any of paragraphs C10-C10.1, wherein the pressure sensor is a threshold pressure sensor configured to indicate whether a pressure in the downstream exceeded a predefined threshold pressure.

C11. The system of any of paragraphs C1-C10.2, further comprising a temperature sensor, optionally a thermocouple or infrared thermometer, configured to measure a temperature of gas in the downstream chamber.

C12. The system of any of paragraphs C1-C11, further comprising the sensor system of any of paragraphs A1-A21.

C12.1. The system of paragraph C12, wherein the sensor system is configured to measure a composition of gas discharged from the combustion arrester into the downstream chamber.

C12.2. The system of any of paragraphs C12-C12.1, wherein the sensor system is configured to measure a composition of gas in the downstream chamber.

C13. The use of any of the systems of paragraphs C1-C12.2 to determine an effectiveness of the combustion arrester.

D1. A method of testing a combustion arrester, the method comprising:

assembling an upstream chamber to define a convergent duct;

assembling a downstream chamber;

fluidically connecting the upstream chamber to the downstream chamber via a combustion arrester, wherein the convergent duct converges towards the combustion arrester and terminates at the combustion arrester;

filling the upstream chamber, the combustion arrester, and the downstream chamber with a flammable gas;

igniting the flammable gas in the upstream chamber;

determining whether the flammable gas in the downstream chamber ignited in response to igniting the flammable gas in the upstream chamber.

D2. The method of paragraph D1, wherein the assembling the upstream chamber includes selecting a number of modular upstream shell sections to define a desired upstream volume within the upstream chamber.

D3. The method of any of paragraphs D1-D2, wherein assembling the downstream chamber includes selecting a number of modular downstream shell sections to define a desired downstream volume within the downstream chamber.

D4. The method of any of paragraphs D1-D3, wherein assembling the upstream chamber and assembling the downstream chamber together include selecting a volume ratio of the upstream chamber to the downstream chamber to simulate predefined combustion conditions.

D5. The method of any of paragraphs D1-D4, further comprising installing an ignition source at a location along the upstream chamber to simulate predefined combustion conditions and wherein igniting the flammable gas includes igniting the flammable gas with the ignition source.

D6. The method of any of paragraphs D1-D5, wherein assembling the upstream chamber includes defining a closed upstream volume with the upstream chamber before igniting the flammable gas.

D7. The method of any of paragraphs D1-D6, wherein assembling the downstream chamber includes defining a closed downstream volume with the downstream chamber before igniting the flammable gas.

D8. The method of any of paragraphs D1-D7, wherein filling the upstream chamber, the combustion arrester, and the downstream chamber includes filling as described in any of paragraphs B1-B12.4.

D9. The method of any of paragraphs D1-D8, wherein determining whether the flammable gas in the downstream chamber ignited includes measuring and/or quantifying (the composition of gas, the temperature, the velocity, and/or the pressure) as described in any of paragraphs B1-B12.4.

D10. The method of any of paragraphs D1-D9, further comprising repeating the method of any of paragraphs D1-D9 with a different upstream volume, a different downstream volume, a different flammable gas, a different ignition source, a different ignition source location, a different pressure, and/or a different temperature.

E1. A kit for assembling a combustion arrester test system, the kit comprising:

a hierarchical series of modular upstream shell sections, wherein each of the modular upstream shell sections includes a section ignition port and wherein at least one of the modular upstream shell sections is configured to define a convergent duct;

a series of modular downstream shell sections;

a turbulence structure;

an ignition source configured to fit into the section ignition ports; and a combustion arrester.

E2. The kit of paragraph E1, wherein at least one, optionally each, of the modular upstream shell sections includes a gas port.

E3. The kit of any of paragraphs E1-E2, further comprising a flammable gas source.

E4. The kit of any of paragraphs E1-E3, wherein the modular upstream shell sections, the modular downstream shell sections, the turbulence structure, the ignition source, the flammable gas source, and/or the combustion arrester is/are as described in any of paragraphs A1-A21 or any of paragraphs C1-C12.2.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entities in the list of entities, and is not limited to at least one of each and every entity specifically listed within the list of entities. For example, "at least one of A and B" (or, equivalently, "at least one of A or B," or, equivalently, "at least one of A and/or B") may refer to A alone, B alone, or the combination of A and B.

As used herein, the singular forms "a", "an" and "the" may be intended to include the plural forms as well, unless the context clearly indicates otherwise.

The various disclosed elements of systems and steps of methods disclosed herein are not required of all systems and methods according to the present disclosure, and the present disclosure includes all novel and non-obvious combinations and subcombinations of the various elements and steps disclosed herein. Moreover, any of the various elements and steps, or any combination of the various elements and/or steps, disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

The invention claimed is:

1. A method of quantifying combustion arrester performance, the method comprising:
    filling an upstream volume and a combustion arrester with a flammable gas;
    igniting the flammable gas in the upstream volume, upstream of the combustion arrester;
    measuring a composition of gas discharged from the combustion arrester, downstream of the combustion arrester, after igniting the flammable gas; and
    based on the composition of the gas measured, quantifying a non-binary quantification of the effectiveness of the combustion arrester stopping a combustion front associated with igniting the flammable gas.

2. The method of claim 1, wherein measuring the composition includes measuring a quantity related to an amount of a combustion species in the gas discharged from the combustion arrester.

3. The method of claim 2, wherein measuring the quantity includes measuring the quantity related to the amount of the combustion species that is one of a hydroxyl radical, water, carbon dioxide, carbon monoxide, formaldehyde, nitric oxide, nitrous oxide, hydrogen, methanol, and a hydrocarbon fuel.

4. The method of claim 1, wherein measuring the composition includes measuring a cross-sectional composition profile of the gas discharged from the combustion arrester.

5. The method of claim 1, wherein measuring the composition includes measuring the composition of the gas without interfering with gas flow from the combustion arrester.

6. The method of claim 1, wherein measuring the composition includes optically interrogating the gas discharged from the combustion arrester.

7. The method of claim 1, wherein measuring the composition includes measuring the composition of the gas by one or more of planar laser-induced fluorescence, laser-induced fluorescence, laser-excited atomic fluorescence, and Fourier transform infrared spectroscopy.

8. The method of claim 1, wherein measuring the composition includes measuring the composition of the gas by one or more of mass spectrometry, gas chromatography, and gas chromatography mass spectrometry.

9. The method of claim 1, further comprising measuring a temperature of the gas discharged from the combustion arrester and wherein quantifying includes quantifying the non-binary quantification of the effectiveness of the combustion arrester stopping the combustion front associated with igniting the flammable gas based on the temperature of the gas discharged from the combustion arrester.

10. The method of claim 9, wherein measuring the temperature includes measuring the temperature by coherent anti-Stokes Raman spectroscopy.

11. The method of claim 1, wherein filling the upstream volume includes filling an upstream chamber that defines the upstream volume, the combustion arrester, and a downstream chamber with the flammable gas, and includes equalizing temperature of the flammable gas, the upstream chamber, the combustion arrester, and the downstream chamber, before igniting the flammable gas.

12. The method of claim 1, wherein filling the upstream volume includes filling an upstream chamber that defines the upstream volume, the combustion arrester, and a downstream chamber with the flammable gas, wherein the upstream volume is a closed volume of the upstream chamber before igniting the flammable gas, and wherein the downstream chamber defines a closed downstream volume before igniting the flammable gas.

13. A system for quantifying combustion arrester performance, the system comprising:
   a combustion arrester having an upstream end and a downstream end;
   an ignition source upstream from the combustion arrester;
   a sensor system with a sensed volume at the downstream end of the combustion arrester, the sensor system configured to measure a composition of gas discharged from the downstream end of the combustion arrester; and
   a controller configured to quantify, based on the composition of gas measured by the sensor system, a non-binary quantification of the effectiveness of the combustion arrester stopping a combustion front.

14. The system of claim 13, wherein the sensor system is configured to measure a quantity related to an amount of a combustion species in the gas discharged from the downstream end of the combustion arrester.

15. The system of claim 13, wherein the sensor system is configured to measure a cross-sectional composition profile of the gas discharged from the downstream end of the combustion arrester.

16. The system of claim 13, wherein the sensor system includes at least one of a planar laser-induced fluorescence apparatus, a laser-induced fluorescence apparatus, a laser-excited atomic fluorescence apparatus, an optical spectrometer, and a Fourier transform infrared spectrometer.

17. The system of claim 13, wherein the sensor system includes at least one of a mass spectrometer, a gas chromatograph, and a gas chromatography mass spectrometer.

18. A system for quantifying combustion arrester performance, the system comprising:
   a combustion arrester having an upstream end and a downstream end;
   an ignition source upstream from the combustion arrester; and
   a sensor system with a sensed volume at the downstream end of the combustion arrester, the sensor system configured to measure a composition of gas discharged from the downstream end of the combustion arrester;
   wherein the sensor system is configured to:
      measure a first quantity related to a first amount of a transient combustion species in the gas discharged from the downstream end of the combustion arrester;
      measure a second quantity related to a second amount of a stable combustion species in the gas discharged from the downstream end of the combustion arrester; and
      based on the first quantity and the second quantity, quantify a non-binary quantification of the effectiveness of the combustion arrester stopping a combustion front.

19. The system of claim 18, wherein the sensor system includes a planar laser-induced fluorescence apparatus configured to measure the first quantity related to the first amount of the transient combustion species.

20. The system of claim 18, wherein the sensor system includes a gas chromatograph configured to measure the second quantity related to the second amount of the stable combustion species.

21. A method of quantifying combustion arrester performance, the method comprising:
   filling an upstream volume and a combustion arrester with a flammable gas;
   igniting the flammable gas in the upstream volume, upstream of the combustion arrester;
   measuring a composition of gas discharged from the combustion arrester, downstream of the combustion arrester, after igniting the flammable gas;
   measuring a temperature of the gas discharged from the combustion arrester; and
   quantifying a performance of the combustion arrester based on the composition of gas measured and based on the temperature of the gas discharged from the combustion arrester.

22. The method of claim 21, wherein measuring the temperature includes measuring the temperature by coherent anti-Stokes Raman spectroscopy.

* * * * *

UNITED STATES PATENT AND TRADEMARK OFFICE
CERTIFICATE OF CORRECTION

PATENT NO. : 10,286,241 B2  
APPLICATION NO. : 15/472039  
DATED : May 14, 2019  
INVENTOR(S) : Jason Scott Damazo et al.

Page 1 of 1

It is certified that error appears in the above-identified patent and that said Letters Patent is hereby corrected as shown below:

On the Title Page

Column 1, Item (73) Assignee:
Insert --; King Abdullah University of Science and Technology, Thuwal (SA)-- after "The Boeing Company, Chicago, IL (US)"

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*